United States Patent [19]
Olson

[11] Patent Number: 4,704,478
[45] Date of Patent: Nov. 3, 1987

[54] PROCESS FOR THE CONDENSATION OF KETONES

[75] Inventor: Kurt D. Olson, Cross Lanes, W. Va.

[73] Assignee: Union Carbide Corporation, Danbury, Conn.

[21] Appl. No.: 878,268

[22] Filed: Jun. 25, 1986

[51] Int. Cl.⁴ .............................................. C07C 45/72
[52] U.S. Cl. .................................. 568/388; 568/391; 568/345; 568/313
[58] Field of Search ............... 568/461, 463, 462, 460, 568/464, 465, 388, 390, 391, 345, 313

[56] References Cited

U.S. PATENT DOCUMENTS

| | | | |
|---|---|---|---|
| 3,728,408 | 4/1973 | Tobias | 568/376 |
| 4,049,571 | 9/1977 | Nissen et al. | 568/390 |
| 4,212,825 | 7/1980 | Nissen et al. | 568/313 |
| 4,239,657 | 12/1980 | Nissen et al. | 568/390 |
| 4,310,440 | 1/1982 | Wilson et al. | 208/135 |
| 4,433,174 | 2/1984 | Hogen | 568/463 |
| 4,440,871 | 4/1984 | Lok et al. | 502/214 |
| 4,476,324 | 10/1984 | Reichle | 568/313 |
| 4,500,651 | 2/1985 | Lok et al. | 502/162 |
| 4,554,143 | 11/1985 | Messina et al. | 502/150 |
| 4,567,029 | 1/1986 | Wilson et al. | 502/150 |

*Primary Examiner*—James H. Reamer
*Attorney, Agent, or Firm*—Gerald L. Coon

[57] ABSTRACT

Two ketone molecules (which can be the same or different) can be condensed together in the presence of hydrogen to produce a higher ketone by contacting the materials to be condensed with a hydrogenation catalyst and with a non-zeolitic molecular sieve, which has in its calcined form an adsorption of isobutane of at least about 2 percent by weight of the non-zeolitic molecular sieve at a partial pressure of 500 torr and a temperature of 20° C. One or both ketones may be generated in situ by dehydrogenation of an alcohol. The non-zeolitic molecular sieves can achieve improved conversions and selectivities as compared with most conventional catalysts for the reaction.

61 Claims, No Drawings

PROCESS FOR THE CONDENSATION OF KETONES

FIELD OF THE INVENTION

This invention relates to a process for the condensation of ketones. More specifically, this invention relates to a process for the condensation of two molecules of ketone (which may be the same or different) in the presence of hydrogen to yield a saturated higher ketone.

BACKGROUND OF THE INVENTION

It is known that various homogeneous catalysts or heterogeneous catalysts which possess either acidic or basic sites catalyze the so-called aldol condensation of ketones to give higher molecular weight ketones. In this condensation, the carbon atom bearing the oxo group in a first ketone molecule acts as an electrophile and attacks the carbon atom alpha to the oxo-bearing carbon atom in a second ketone molecule, with removal of a hydrogen atom from the alpha carbon atom of the second compound and protonation of the oxo oxygen atom in the first compound. The reaction may be run in the presence of hydrogen and of a hydrogenation catalyst to give a saturated ketone. For example carrying out the aldol condensation of acetone in the presence of hydrogen and of a hydrogenation catalyst will yield methyl isobutyl ketone (MIBK), as the final product.

The aldol condensation is a useful reaction for the production of higher ketones from lower, readily avalable ketones, and is extensively used for this purpose in the organic chemical industry. Acetone derivatives alone, most of which are prepared by some variant of an aldol condensation, make up a market of about 500 million pounds annually. Methyl isobutyl ketone (MIBK) alone makes up a major portion of the acetone derivatives market with about 200 million pounds produced annually. However, one difficulty frequently experienced in the use of the aldol condensation is its tendency to produce complex mixtures of products. The only structural requirements on the two condensing ketone molecules, apart from the presence of their oxo groups, is that the first ketone molecule possess at least one hydrogen atom on the carbon atom alpha to the oxo group. Since the product of the condensation is itself a ketone and normally has at least one hydrogen atom on the carbon atom alpha to the oxo group, the condensation product can undergo further condensation to produce additional products. Thus, depending on the catalyst and reaction conditions employed, the initial products of the condensation can react with more of the starting materials or with themselves to form oligomeric species or they can cyclize to form cyclic aliphatic or aromatic products. For example the MIBK initially produced by self-condensation of acetone in the presence of hydrogen can undergo further condensation with acetone to give diisobutyl ketone (DIBK).

In most aldol condensations it is, for economic reasons, desirable to optimize the production of only one of the numerous possible products. In a few cases, it may be desired to isolate more than one product (for example, the aldol condensation of acetone is used industrially to produce both MIBK and DIBK, both of which are of commercial value and these two ketones are easily separable by fractional distillation), but even in these cases it is desirable to be able to control the relative amounts of the products in order to match these relative amounts to market demands. Thus, catalysts which selectively catalyze the formation of selected ones of the numerous possible products greatly improve the commercial use of the aldol condensation.

Because molecular sieves can affect product distribution by shape selectivity, that is they can curtail the formation of products that do not have the proper shape to enter into or exit from the molecular sieve pores, they offer the opportunity to tailor the product distribution from an aldol condensation to maximize production of the desired products by appropriate choices of the molecular sieve catalyst and/or reaction conditions. Accordingly, several attempts have been made to use molecular sieves as catalysts in aldol condensations.

U.S. Pat. No. 4,339,606 issued July 13, 1982 to Huang et al. and assigned to Mobil Oil Corporation describes the use of palladium loaded ZSM-5 zeolite as a catalyst for the self-condensation of acetone under hydrogen at 600 psi. and 180° C. to give MIBK. This patent claims a 98% selectivity to MIBK and no DIBK production but we have been unable to eliminate DIBK production using catalysts of similar pore size, composition or structure.

Golodets, G. I.; Pavlenko, N. V.; Korzhova, L. F.; Vaisberg, K. M.; Churkin, Yu. I., Kinet. Katal., 1984, 25, 1015 report the self-condensation of acetone metal-containing zeolites to give a mixture of products. Sumitomo Chemical Co. Ltd., German Offenlegungsschrift 1936203, published 20 July 1968, and British Pat. No. 1,252,335 published 3 November, Showa Denko K.K., Japanese Patent Application No. 72/13017 filed 20 Apr. 1972, Application No. 73/27288 filed 21 Aug. 1973, Application No. 73/27287 filed 21 Aug. 1973, and Application No. 73/26736 filed 15 Aug. 1973 report similar reactions.

U.S. Pat. No. 3,728,408 issued 17 Apr. 1973 to Tobias, U.S. Pat. No. 4,011,278 issued 8 May 1977 to Plank, Rosinski and Kerr, and U.S. Pat. No. 4,306,106 issued 15 Dec. 1981 to Kerr, Plank and Rosinski, all assigned to Mobil Oil Corporation, disclose by way of example the aldol condensation of acetone over aluminosilicate zeolites to give mesityl oxide and mesitylene but the catalyst contains no hydrogenation site. These reactions are also discussed in Chang, C. D.; Lang, W. H.; Smith, R. L., J. Catal, 1979, 56, 169 and Chang, C. D.; Silvestri, A. J., J. Catal, 1977, 47, 249, and are reviewed in Chang, C. D.; Lang, W. H.; Bell, W. K. in "Catalysis of Organic Reactions", Moser, W. R. (Ed.), Marcel Dekker: New York, 1981, pp 73–94.

The following papers:

Kuznetsov, O. I.; Shauki, M. Kh.; Panchekov, G. M., Khim, Kinet, Katal, 1979, 182;

Guseinov, A. D.; Chasova, T. A.; Kuznetsov, A. I.; Panchenkov, G. M., Neft. Gaz. (Vinogradov, V. N. Ed.), 1974, 146;

Kuznetsov. O. I.; Panchenkov, G. M.; Chasova, T. A.; Guseinov, A. D., Neftepererab. NeftKhim. (Moscow), 1973, 44;

Kuznetsov, A. I.; Panchenkov, G. M.; Guseinov, A. M.; Chasova, T. A., Neftpererab. NeftKhim. (Moscow), 1973, 28;

Isakov, Ya. I.; Minachev, Kh. M.; Usachev, N. Ya., Izv. Akad. Nauk. SSSR, Ser. Khim., 1972, 1175;

Grigor'ev, A. A.; Guseva, S. I.; Pinkhasik, E. V.; Avrekh, G. L.; Sedlyarov, V. A.; Lunin, A. f., Khim. Prom-st. (Moscow), 1981, 73; and Guseva, S. I.; Grigor'ev, A. A.; Pinkhasik, E. V.; Avrekh, G. L., Neftpererab. NefteKhim. (Moscow), 1979, 45, examine the condensation of acetone over traditional zeolites such as A, X, or Y zeolites but these materials show rather poor activity, selectivity and lifetime.

U.S. Pat. No. 4,433,174 issued 21 Feb. 1984 and U.S. Pat. No. 4,447,641 issued 8 May 1984, both to Hagen and both assigned to Standard Oil Company (Indiana) discuss the condensation of aldehydes or esters with formaldehyde to give alpha, beta unsaturated aldehydes or esters, respectively, using borosilicate molecular sieves as catalysts. Again, no hydrogenation takes place in these processes. U.S. Pat. No. 4,374,274 issued 15 Feb. 1983 to Hellen, Halbritter and Gramlich, and assigned to BASF describes the use of a palladium on metal phosphate catalyst to effect the condensation of ketones with formaldehyde under hydrogen to give methyl substituted ketones, but this catalyst is not a molecular sieve based catalyst.

Dworezkov et al., "Absorptive properties of aluminumphosphate molecular sieves", in Che and Bond (eds.), Adsorption and catalysis on oxide surfaces (Studies in Surface Science and Catalysis 21), pp. 163-172, (Elsevier, Amsterdam, 1985), discloses the adsorption of acetone on to the aluminophosphate AlPO$_4$-5 and subsequent desorption of mesityl oxide and other materials from the aluminophosphate.

It is also known that the closely related Knoevenagel condensation occurs over molecular sieves; see Taylor, G. A., J. Chem. Soc., Perkin Trans. I., 1981, 3132.

None of the molecular sieve catalysts described above are ideal for use in aldol condensations. In particular, some of the prior art molecular sieve catalysts frequently fail to achieve high selectivities to the desired products of aldol condensations when operated at the conversion rates required in industrial operation.

It has now been discovered that the use of certain non-zeolitic molecular sieves as catalysts in aldol condensations offers high selectivities and these high selectivities can be maintained at high conversions.

SUMMARY OF THE INVENTION

This invention provides a process for condensing a first ketone with a second ketone; the two ketones may be different or may be the same. In the process of the present invention, the first and second ketones are contacted, in the presence of hydrogen gas, with a non-zeolitic molecular sieve, the non-zeolitic molecular sieve having, in its calcined form, an adsorption of isobutane of at least about 2 percent by weight of the non-zeolitic molecular sieve at a partial pressure of 500 torr and a temperature of 20° C., and with a hydrogenation catalyst capable of catalyzing the hydrogenation of an ethylenic unsaturation in an ethylenically unsaturated ketone. The hydrogenation catalyst may optionally be incorporated into the non-zeolitic molecular sieve. The contacting of the ketones with the hydrogenation catalyst and the non-zeolitic molecular sieve is effected under conditions effective to cause condensation of the ketones and reaction with the hydrogen to form a saturated ketone.

DETAILED DESCRIPTION OF THE INVENTION

The non-zeolitic molecular sieves used in the process of the present invention comprise a large number of aluminophosphates and aluminosilicophosphates having a variety of crystal structures, which may include one or more other elements in addition to aluminum, phosphorus and silicon. Accordingly, the manner in which these non-zeolitic molecular sieves are used in the process of the present invention will first be described, and thereafter the chemical nature, and methods for the preparation, of the non-zeolitic molecular sieves will be described.

PROCESS OF THE INVENTION

As already mentioned, in the process of the present invention the ketones are contacted with a non-zeolitic molecular sieve having, in its calcined form an adsorption of isobutane of at least about 2 percent by weight of the non-zeolitic molecular sieve at a partial pressure of 500 torr and a temperature of 20° C. These adsorption characteristics ensure that the non-zeolitic molecular sieve has a pore size sufficiently large to effect catalysis of the condensation reaction. Desirably, the non-zeolitic molecular sieve has, in its calcined form, an adsorption of isobutane of at least about 4 percent by weight of the non-zeolitic molecular sieve at a partial pressure of 500 torr and a temperature of 20° C.

A wide variety of ketones may be condensed using the process of the present invention. However, because of their ready availability and low cost, and because the rate at which is aldol condensation proceeds is governed in part by the ability of the reactants and/or products to enter into or exit from the pores of the non-zeolitic molecular sieve catalyst, the process of the present invention is preferably conducted using ketones containing three or four carbon atoms. Thus, for example, the process of the present invention may be used for the condensation of, inter alia, acetone and methyl ethyl ketone.

The process of the present invention may be conducted with the reactants in the liquid phase. However, it is preferred that the process of the present invention be conducted as a heterogeneous, gas phase reaction with the reactants in the gaseous phase, since a gas phase reaction can be run at higher temperatures under moderate pressures (typically from one to a few atmospheres) using comparatively inexpensive apparatus.

In a gas phase process, the reactants may be mixed with an inert carrier gas (such as nitrogen) while being contacted with the non-zeolitic molecular sieve; however the use of such a carrier gas is not necessary in the process of the present invention, especially since the hydrogen gas, although a reactant, also acts as a carrier gas for the other reactants. The degree of dilution of the reactants with such an inert carrier gas may vary considerably depending upon the selectivity to, and the output of, the product required.

Selection of the temperature and pressure at which the process of the present invention is to be conducted is usually involves a compromise between selectivity to the desired product and throughput of a given reactor. Increasing the reaction temperature increases the reaction rate, and hence the conversion achieved in a single pass through a given reactor, but tends to reduce selectivity. Accordingly, it is recommended that the process of the present invention be conducted at a temperature not in excess of about 350° C., and preferably in the range of about 150° C. to about 300° C. For many reactions, the optimum temperature appears to be about 200° C.

The process of the present invention produces, as its product a saturated ketone; for example, the self-condensation of acetone in the presence of hydrogen yields significant amounts of methyl isobutyl ketone (4-methylpentan-2-one). The hydrogenation catalyst used in the process of the present invention may be any of those catalysts conventionally used in the art for the hydrogenation of olefinic linkages. For example, the hydrogenation catalyst may be copper, nickel, cobalt, palladium, platinum, rhodium or iridium. Preferred metals for the hydrogenation catalyst are palladium, platinum and nickel. Although it is possible to physically mix the hydrogenation catalyst with the non-zeolitic molecular sieve, it is preferred that the hydrogenation catalyst be incorporated into the non-zeolitic molecular sieve. Incorporation of the hydrogenation catalyst into the non-zeolitic molecular sieve can be effected by any of the methods used in the prior art to load molecular sieves with reduced or oxidized metals. For example, an appropriate salt of the catalytic metal (e.g. tetraamine palladium(II) chloride in the case of palladium) can be dissolved in water or another solvent and this solution used to impregnate the non-zeolitic molecular sieve. Optionally, calcination under air, oxygen, hydrogen or an inert gas may be used to enhance the activity of the catalyst. Other techniques, such as ion-exchange, can also be used to load the catalytic metal into the non-zeolitic molecular sieve.

The preferred level of metal loading depends upon the metal used. In the case of palladium, for example, only small amounts are needed to ensure hydrogenation. Palladium levels as low as 0.02% by weight of the non-zeolitic molecular sieve have been shown to be active. Desirably, a palladium-loaded non-zeolitic molecular sieve comprises from about 0.01 to about 5, and preferably from 0.1 to about 1, percent by weight of palladium metal. Since copper is a less active hydrogenation catalyst than palladium, larger amounts of copper should be incorporated to ensure efficient hydrogenation; typically, a copper-loaded non-zeolitic molecular sieve should contain about 5 to about 10% by weight of copper metal.

The process of the present invention can be conducted using as starting materials the two ketones to be condensed with one another. However, the process of the present invention can also be conducted by forming at least one of the ketones in situ by feeding to the process a precursor compound capable of being converted to the ketone and providing a precursor catalyst effective, under the reaction conditions, to convert the precursor compound to the desired ketone. Desirably, the precursor compound comprises a compound capable of being dehydrogenated to yield the ketone, and the precursor catalyst comprises a dehydrogenation catalyst. Thus, the precursor compound may be a secondary alcohol, such as isopropanol, which is dehydrogenated to form a ketone.

The alcohol dehydrogenation component could in theory be the same catalyst employed to catalyze the condensation reaction, especially when this catalyst is a metal-loaded, combined condensation/hydrogenation catalyst, since the metals employed for the hydrogenation of olefinic linkages are sometimes known to catalyst the dehydrogenation of alcohols to produce aldehydes and ketones. However, experiments to date have indicated that metal-loaded non-zeolitic molecular sieves which are effective aldol condensation and olefin hydrogenation catalysts do not appear to be effective catalysts for the dehydrogenation of alcohols to ketones. Accordingly, when it is desired to conduct the process of the present invention starting from an alcohol, it is preferred to use two separate catalysts, the first of which catalyzes the conversion of the alcohol to the ketone, and the second of which is the non-zeolitic molecular sieve which catalyzes the condensation to yield the ketone product. Optionally, the two catalysts are arranged sequentially in the reactor with the non-zeolitic molecular sieve downstream from the dehydrogenation catalyst. Catalysts for the dehydrogenation of alcohols to ketones are available commercially, for example the commercial copper chromite catalyst sold as Harshaw Catalyst Cu-0203-T-⅛.

When the procss of the present invention is conducted starting from a precursor compound which is dehydrogenated to produce the ketone used in the aldol condensation itself, the hydrogen generated by the dehydrogenation of the precursor compound is reincorporated into the condensation product. Accordingly, the use of a precursor compound in this manner reduces or eliminates the need for supplying hydrogen gas from an external source. For example, in such a process, the precursor compound may be isopropanol and the final product of the condensation methyl isobutyl ketone and/or diisobutyl ketone.

One preferred use for the process of the present invention is the self-condensation of acetone; this self-condensation yields methyl isobutyl ketone and/or diisobutyl ketone. This reaction can be run conveniently at temperatures of from about 150° C. to about 350° C. and at pressures from atmospheric to about 1000 psig., preferably at about 200° to 275° C. at atmospheric pressure for ease of operation. Higher temperatures led to the formation of more by-products (i.e. products other than MIBK and DIBK), and in some cases the formation of significant amounts of propane and/or diisopropyl ether was noted among these by-products, while lower temperatures generally gave reduced conversions. Higher pressures generally led to the formation of more DIBK at the expense of the more desirable MIBK. The condensation may be conducted at weight hourly space velocities of liquid acetone in the range of from about 0.1 to about 50, preferably from about 0.5 to about 5.0. Under optimum conditions, MIBK:DIBK ratios of as high as 20:1 have been observed at 10% acetone conversion and with an overall combined selectivity to MIBK and DIBK of greater than 98%. By appropriate adjustment of reaction conditions, the MIBK:DIBK ratio can be adjusted over a wide range, thereby enabling the process of the present invention to be closely matched to market demand for the two products, thus maximizing the economic return from the process. This represents a significant advance over prior art molecular sieve catalysts for this reaction; prior art molecular sieve catalysts have in general produced too many by-products for optimum economic efficiency of the process. In addition, the total selectivity to MIBK and DIBK observed using the process of the present invention under optimum conditions is greater than that achieved by most prior art molecular sieve catalysts.

As already discussed above, the self-condensation of acetone may be effected using generation of the acetone in situ by dehydrogenation of isopropanol.

As with all processes employing molecular sieve catalysts, the process of the present invention may eventually be affected by deactivation of the non-zeolitic molecular sieve catalyst due to coking and similar processes. If such deactivation does occur, the activity of the catalyst can be restored by heating in air at elevated temperatures; typically heating the catalyst in air at 500° C. for about two hours will completely restore the activity of the catalyst. Empirically it has been found that the non-zeolitic molecular sieves can be used in the process of the present invention for extended period without deactivation. The resistance to deactivation of this catalyst compares favorably with that of molecular sieve catalysts used in prior art aldol condensations.

The non-zeolitic molecular sieves may be modified by depositing or impregnating the non-zeolitic molecular sieve with cations, anions or salts so as to improve its efficacy as a catalyst in the process of the present invention. Techniques which may be employed to effect the deposition or impregnation of a non-zeolitic molecular sieve are generally known in the art. Such procedures may involve such procedures as (1) impregnating the non-zeolitic molecular sieve with a solution comprising a solvent or solubilizing agent of one or more such modifying materials in an amount sufficient to deposit the desired weight of such materials in the non-zeolitic molecular sieve and/or (2) exchanging the non-zeolitic molecular sieve with a solution containing the modifying material. The impregnation or deposition of the modifying materials may generally be accomplished by heating the non-zeolitic molecular sieve at an elevated temperature to evaporate any liquid present to effect deposition or impregnation of the modifying material on to the interior and/or exterior surface of the non-zeolitic molecular sieve, or by the exchange of cations present in the non-zeolitic molecular sieve with cations that provide for the desired properties. Alternatively, the modifying material may be formed on the non-zeolitic molecular sieve from an emulsion or slurry containing the modifying material by heating the non-zeolitic molecular sieve. Impregnation or exchange procedures are generally the preferred techniques because they utilize and introduce the modifying material more efficiently than other procedures such as coating procedures since a coating procedure is generally not able to effect substantial introduction of the modifying material on to the interior surfaces of the non-zeolitic molecular sieve. In addition, coated materials are more generally susceptible to the loss of the modifying materials by abrasion.

Suitable modifying materials include alkali metals, alkaline earth metals, transition metals and the salts thereof including inorganic and organic salts such as nitrates, halides, hydroxides, sulfates and carboxylates. Other modifying materials generally employed in the art are also believed to be employable in the non-zeolitic molecular sieves.

In carrying out the process of the present invention, the non-zeolitic molecular sieves may be admixed (blended) or provided sequentially to other materials which may provide some property which is beneficial under process conditions, such as improved temperature resistance or improved catalyst life by minimization of coking, or which are simply inert under the process conditions used. Such materials may include synthetic or naturally-occurring substances as well as inorganic materials such as clays, silicas, aluminas, crystalline aluminosilicate zeolites, metal oxides and mixtures thereof. In addition, the non-zeolitic molecular sieves may be formed with materials such as silica, alumina, silica-alumina, silica-magnesia, silica-zirconia, silica-thoria, silica-berylia, and silica-titania, as well as ternary compositions, such as silica-alumina-thoria, silica-alumina-zirconia and clays present as binders. The relative proportions of the above materials and the non-zeolitic molecular sieves may vary widely with the non-zeolitic molecular sieve content ranging between about 1 and about 99 percent by weight of the composite.

The following Examples are provided to further illustrate the process of the present invention, but are not limitative thereof.

EXAMPLES

The following Examples illustrate the use of ALPO$_4$-31, SAPO-5, SAPO-11, SAPO-41, CoAPSO-11, MgAPO-36, MnAPSO-11, TiAPSO-5 and FeAPSO-5 in the process of the present invention. The characteristic X-ray tables for SAPO-11 and SAPO-41 are given in the description of the non-zeolitic molecular sieves below. The ALPO$_4$-31 was produced as described in U.S. Pat. No. 4,310,440, Example 54. The characteristic X-ray tables for the other non-zeolitic molecular sieves used in the following Examples are as follows:

| 2θ | d(Å) | Relative Intensity |
|---|---|---|
| SAPO-5 | | |
| 7.35–7.65 | 12.0–11.56 | m–vs |
| 19.6–19.95 | 4.53–4.46 | m |
| 20.9–21.3 | 4.25–4.17 | m–vs |
| 22.3–22.6 | 3.99–3.93 | m–vs |
| 25.85–26.15 | 3.46–3.40 | w–m |
| CoAPSO-11 | | |
| 7.9–8.1 | 11.19–10.92 | m |
| 9.3–9.5 | 9.51–9.31 | m–s |
| 21.0–21.3 | 4.23–4.17 | vs |
| 22.1–22.3 | 4.02–3.99 | m |
| 22.7–23.1 | 3.92–3.85 | m |
| 23.2–23.4 | 3.83–3.80 | m |
| MnAPSO-11 | | |
| 9.4–9.8 | 9.41–9.03 | m |
| 16.1–16.2 | 5.50–5.47 | vs–m |
| 21.0–21.5 | 4.23–4.13 | m–vs |
| 22.1–22.2 | 4.02–4.00 | m |
| 22.4–22.5 | 3.97–3.95 | m–s |
| 23.1–23.5 | 3.85–3.79 | m |
| TiAPSO-5 | | |
| 7.3–7.5 | 12.11–11.79 | s–vs |
| 19.7–19.9 | 4.51–4.46 | m |
| 20.9–21.0 | 4.25–4.23 | m–s |
| 22.3–22.5 | 3.99–3.95 | m–vs |
| 25.8–26.1 | 3.453–3.411 | m |
| 28.9–29.1 | 3.089–3.069 | w–m |
| FeAPSO-5 | | |
| 7.3–7.5 | 12.11–11.79 | m–vs |
| 14.8–14.95 | 5.99–5.93 | w–m |
| 19.6–19.8 | 4.53–4.48 | m |
| 21.0–21.2 | 4.23–4.19 | m |
| 22.35–22.5 | 3.98–3.95 | m–vs |
| 25.8–25.95 | 3.453–3.434 | w–m |
| MgAPO-36 | | |
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

Experimental Conditions

The various non-zeolitic molecular sieve catalysts were prepared as described below and then calcined for at least one hour under nitrogen at the reaction temperature prior to use. When necessary, between successive runs, the catalysts were regenerated by calcination in air at 500° C.

The catalysts were metal-loaded by incipient wetness pore loading by evacuating a flask containing the molecular sieve and adding one pore volume of water into which was dissolved the necessary amount of tetraammine palladium(II) chloride, nickel acetate, copper acetate or cesium chloride necessary to give the desired metal loading. The solution was absorbed by the molecular sieve. The material was then calcined for at least 4 hours under air at 500° to 550° C.

All the condensations were conducted using a micro reactor consisting of a ⅜ inch (9 mm.) diameter straight tube encased in a 1 inch (25 mm.) diameter sheath of stainless steel heated with an electric split furnace. With the powdered catalysts, approximately 1 gram of catalyst was dispersed among about 4 grams of 20–30 U.S. mesh quartz chips and placed in the heated zone of the reactor. Connected to the inlet of the reactor were a source of hydrogen and a liquid feed line containing liquid acetone; this liquid feed line was connected to a high pressure liquid chromatography (HPLC) type solvent pump. The products of the reaction were collected immediately downstream from the reactor in a cold trap kept at 0° C. Gas chromatographic analysis of the reactor off gas downstream from the cold trap indicated that virtually all of the products of the reaction and all the unchanged reactants were collected in the cold trap. The material collected in the cold trap was analyzed by gas chromatography on a 6 foot by ⅛ inch (1523 by 3 mm.) 15% SE-30 (a non-polar silicone fluid) on Chrom W column. The column was operated in a temperature-programmed mode, being maintained at 70° C. for 4 minutes, then raised at 20° C. per minute to 250° C., and finally maintained at 250° C. for 2 minutes. All percentages quoted are based upon the areas under the chromatogram peaks.

The following experiments illustrate the self-condensation of acetone over various non-zeolitic molecular sieves at varying pressures and temperatures. To provide comparisons with processes for aldol condensation using zeolites, similar experiments (indicated by "(Control)" after the name of the molecular sieve) were conducted using zeolite catalysts under similar conditions. The results are shown in the Table below; in this Table, pressures are psig., "atm" denotes atmospheric pressure, temperatures are in 0° C., ratios are by weight and conversions and selectivities are in percent. In Table I, all the catalysts were metal-loaded by incipient wetness pore filling using the technique described above, "Conv" denotes "Conversion" and "Sel" denotes the total selectivity of conversion of acetone to MIBK and DIBK combined. The WHSV was 1.6 hr.$^{-1}$

TABLE I

| Catalyst | Temp | Pressure | Conv | MIBK:DIBK | Sel |
|---|---|---|---|---|---|
| 0.5% Pd—Y-52 (Control) | 200 | atm | 3 | 5:1 | 70$^a$ |
| 0.5% Pd—ELZ-105 (Control) | 200 | atm | 30 | 7:1 | 85$^b$ |
| 0.5% Pd—ELZ-105 (Control) | 200 | 800 | 60 | 6:1 | 75 |
| 0.5% Pd—SAPO-11 | 200 | atm | 20 | 15:1 | 60$^c$ |
| 0.5% Pd—SAPO-41 | 200 | atm | 20 | 15:1 | 60$^c$ |
| 0.5% Pd—SAPO-5 | 200 | atm | 10 | 7:1 | 98 |
| 0.5% Pd—SAPO-5 | 200 | 100 | 30 | 7:1 | 90 |
| 0.5% Pd—SAPO-5 | 200 | 800 | 50 | 7:1 | 85 |
| 0.5% Pd—MnAPSO-11 | 200 | atm | 4 | 25:1 | 70$^d$ |
| 0.5% Pd—TiAPSO-5 | 200 | atm | 4 | 25:1 | 50$^d$ |
| 0.5% Pd—MgAPO-36 | 200 | atm | 6 | 30:1 | 10$^d$ |
| 0.5% Pd—ALPO$_4$-31 | 200 | atm | 10 | 20:1 | 50$^d$ |
| 0.5% Pd—FeAPSO-5 | 200 | atm | 4 | 30:1 | 15$^d$ |

TABLE I-continued

| Catalyst | Temp | Pressure | Conv | MIBK:DIBK | Sel |
|---|---|---|---|---|---|
| 0.5% Pd—CoAPSO-11 | 200 | atm | 6 | 10:1 | 60$^c$ |
| 2.0% Ni—SAPO-5 | 250 | atm | 4 | 20:1 | 30$^c$ |
| 2.0% Ni—SAPO-5 | 250 | atm | 3 | 20:1 | 40$^c$ |

$^a$The catalyst deactivated rapidly.
$^b$The major by-product was mesityl oxide.
$^c$The major by-product was propane.
$^d$The major by-products were diisopropyl ether and propane.

NON-ZEOLITIC MOLECULAR SIEVES

The term "non-zeolitic molecular sieves" or "NZMS" is defined in the instant invention to include the "SAPO" molecular sieves of U.S. Pat. No. 4,440,871, "ELAPSO" molecular sieves as disclosed in U.S. Ser. No. 600,312, filed Apr. 13, 1984, and certain "ALPO$_4$", "MeAPO", "FeAPO", "TAPO" and "ELAPO" molecular sieves, as hereinafter described. Crystalline "ALPO$_4$" aluminophosphates are disclosed in U.S. Pat. No. 4,310,440 issued Jan. 12, 1982; crystalline metal aluminophosphates (MeAPOs were "Me" is at least one of Mg, Mn, Co and Zn) are disclosed in U.S. Pat. No. 4,567,029, issued Jan. 28, 1986; crystalline ferroaluminophosphates (FeAPOs) are disclosed in U.S. Pat. No. 4,554,143, issued Nov. 19, 1985; titanium aluminophosphates (TAPOs) are disclosed in U.S. Pat. No. 4,500,651, issued Feb. 19, 1985; certain non-zeolitic molecular sieves ("ELAPO") are disclosed in EPC Patent Application 85104386.9 (Publication No. 0158976, published Oct. 13, 1985) and 85104388.5 (Publication No. 158349, published Oct. 16, 1985); and ELAPSO molecular sieves are disclosed in copending U.S. Ser. No. 600,312, filed Apr. 13, 1984 (EPC Publication No. 0159624, published Oct. 30, 1985). The aforementioned applications and patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, MeAPO-11 and ELAPSO-31. In the following discussion on NZMSs set forth hereinafter the mole fraction of the NZMSs are defined as compositional values which are plotted in phase diagrams in each of the identified patents, published applications or copending applications.

ELAPSO MOLECULAR SIEVES

"ELAPSO" molecular sieves are described in copending U.S. Ser. No. 600,312, filed Apr. 13, 1984, (EPC Publication No. 0159,624, published Oct. 30, 1985, incorporated herein by reference) as crystalline molecular sieves having three-dimensional microporous framework structures of ELO$_2$, AlO$_2$, PO$_2$, SiO$_2$ oxide units and having an empirical chemical composition on an anhydrous basis expressed by the formula:

mR: $(EL_wAl_xP_ySi_z)O_2$ wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a three dimensional oxide framework, "EL"

being characterized as an element having a mean "T-O" distance in tetrahedral oxide structures between about 1.51 Angstroms and about 2.06 Angstroms, "EL" having a cation electronegativity between about 125 kcal/g-atom to about 310 kcal/gm-atom and "EL" being capable of forming stable M-O-P, M-O-Al or M-O-M bonds in crystalline three dimensional oxide structures having a "M-O" bond dissociation energy greater than about 59 kcal/g-atom at 298° K.; and "w", "x", "y" and "z" represent the mole fractions of "EL", aluminum, phosphorus and silicon, respectively, present as framework oxides, said mole fractions being within the limiting compositional values or points as follows:

| Point | Mole Fraction | | |
|---|---|---|---|
| | x | y | (z + w) |
| A | 0.60 | 0.39–(0.01)p | 0.01(p + 1) |
| B | 0.39–(0.01p) | 0.60 | 0.01(p + 1) |
| C | 0.01 | 0.60 | 0.39 |
| D | 0.01 | 0.01 | 0.98 |
| E | 0.60 | 0.01 | 0.39 | where "p" is an integer corresponding to the number of elements "EL" in the $(El_wAl_xP_ySi_z)O_2$ constituent, The "ELAPSO" molecular sieves are also described as crystalline molecular sieves having three-dimensional microporous framework structures of $ELO_2$, $AlO_2$, $SiO_2$ and $PO_2$ tetrahedral oxide units and having an empirical chemical composition on an anhydrous basis expressed by the formula:

mR: $(EL_wAl_xP_ySi_z)O_2$ wherein "R" represents at least one organic templating agent present in the intracrystalline pore system, "m" represents the molar amount of "R" present per mole of $(EL_wAl_xP_ySi_z)O_2$ and has a value of from zero to about 0.3; "EL" represents at least one element capable of forming a framework tetrahedral oxide and is selected from the group consisting of arsenic, beryllium, boron, chromium, cobalt, gallium, germanium, iron, lithium, magnesium, manganese, titanium and zinc; and "w", "x", "y" and "z" represent the mole fractions of "EL", aluminum, phosphorus and silicon, respectively, present as tetrahedral oxides, said mole fractions being within the limiting compositional values or points as follows:

| Point | Mole Fraction | | |
|---|---|---|---|
| | x | y | (z + w) |
| a | 0.60 | 0.39–(0.01)p | 0.01(p + 1) |
| b | 0.39–(0.01p) | 0.60 | 0.01(p + 1) |
| c | 0.10 | 0.55 | 0.35 |
| d | 0.55 | 0.10 | 0.35 | where "p" is as above defined.

The "ELAPSO" molecular sieves include numerous species which are intended herein to be within the scope of the term "non-zeolitic molecular sieves" such being disclosed in the following copending and commonly assigned applications, incorporated herein by reference thereto [(A) following a serial number indicates that the application is abandoned, while (CIP) following a serial number indicates that the application is a continuation-in-part of the immediately preceding application]::

| U.S. Ser. No. | Filed | NZMS |
|---|---|---|
| 600,174 | April 13, 1984 | CoAPSO |
| 600,173 | April 13, 1984 | FeAPSO |
| 600,180 | April 13, 1984 | MgAPSO |
| 600,175 | April 13, 1984 | MnAPSO |
| 600,179 | April 13, 1984 | TiAPSO |
| 600,170 | April 13, 1984 | ZnAPSO |
| 600,168 | April 13, 1984 | CoMgAPSO |
| 600,182 | April 13, 1984 | CoMnMgAPSO |
| 599,808(A) | April 13, 1984 | AsAPSO |
| 845,484(CIP) | March 31, 1986 | AsAPSO |
| 600,177(A) | April 13, 1984 | BAPSO |
| 845,255(CIP) | March 28, 1986 | BAPSO |
| 600,176(A) | April 13, 1984 | BeAPSO |
| 841,752(CIP) | March 20, 1986 | BeAPSO |
| 599,830(A) | April 13, 1984 | CAPSO |
| 852,174(CIP) | April 15, 1986 | CAPSO |
| 599,925(A) | April 13, 1984 | GaAPSO |
| 845,985(CIP) | March 31, 1986 | GaAPSO |
| 599,971(A) | April 13, 1984 | GeAPSO |
| 852,175(CIP) | April 15, 1986 | GeAPSO |
| 599,952(A) | April 13, 1984 | LiAPSO |
| 847,227(CIP) | April 2, 1986 | LiAPSO |

TiAPSO MOLECULAR SIEVES

The TiAPSO molecular sieves of U.S. Ser. No. 600,179, filed Apr. 13, 1984 have three-dimensional microporous framework structures of $TiO_2$, $AlO_2$, $PO_2$ and $SiO_2$ tetrahedral oxide units having an empirical chemical composition on an anhydrous basis expressed by the formula:

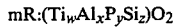

mR:$(Ti_wAl_xP_ySi_z)O_2$ wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

TiAPSO compositions are generally synthesized by hydrothermal crystallization from a reaction mixture containing active sources of titanium, silicon, aluminum and phosphorus, and preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the TiAPSO product are obtained, usually a period of from hours to several weeks. Generally, the crystallization time is from about 2 hours to about 30 days and typically from about 4 hours to about 20 days. The product is recovered by any convenient method such as centrifugation or filtration.

In synthesizing the TiAPSO, it is preferred to employ a reaction mixture composition expressed in terms of the molar ratios as follows:

$$aR:(Ti_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of titanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing titanium, aluminum, phosphorus and silicon as framework tetrahedral oxides are prepared as follows:

Preparative Reagents

TiAPSO compositions are typically prepared using numerous regents. Typical reagents which may be employed and abbreviations employed in U.S. Ser. No. 600,179 for such reagents are as follows:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: 85 weight percent aqueous phosphoric acid;
(d) Tiipro: titanium isopropoxide;
(e) TEAOH: 40 weight percent aqueous solution of tetraethylammonium hydroxide;
(f) $Pr_2NH$: di-n-propylamine, $(C_3H_7)_2NH$;
(g) $Pr_3NH$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$; and
(j) C-hex: cyclohexylamine.

Preparative Procedures

TiAPSOs may be prepared by forming a starting reaction mixture by adding the $H_3PO_4$ and the water. This mixture is mixed and to this mixture aluminum isoproxide is added. This mixture is then blended until a homogeneous mixture is observed. To this mixture the LUDOX-LS is added and the resulting mixture blended (about 2 minutes) until a homogeneous mixture is observed.

The titanium isopropoxide is added to the above mixture and the resulting mixture blended until a homogeneous mixture is observed. The organic templating agent is then added to the resulting mixture and the resulting mixture blended until a homogeneous mixture is observed, i.e., about 2 to 4 minutes. When the organic templating agent is quinuclidine the procedure is modified such that the quinuclidine is dissolved in about one half the water and accordingly the $H_3PO_4$ is mixed with about one half the water. (The pH of the mixture is measured and adjusted for temperature). The mixture is then placed in a lined (polytetrafluoroethylene) lined stainless steel pressure vessel and digested at a temperature (150° C. or 200° C.) for a time or placed in lined screw top bottles for digestion at 100° C. Digestions are typically carried out under autogenous pressure.

The products are removed from the reaction vessel and cooled.

MgAPSO MOLECULAR SIEVES

The MgAPSO molecular sieves of U.S. Ser. No. 600,180, filed Apr. 13, 1984 have three-dimensional microporous framework structures of $MgO_2^-$, $AlO_2^-$, $PO_2^+$ and $SiO_2$ tetrahedral oxide units and have an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value from zero (0) to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MgAPSO compositions are generally synthesized by hydrothermal crystallization for an effective time at effective pressures and temperatures from a reaction mixture containing reactive sources of magnesium, silicon, aluminum and phosphorus, an organic templating, i.e., structure-directing, agent, preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the MgAPSO product are obtained, usually a period of from several hours to several weeks. Generally, the crystallization period will be from about 2 hours to about 30 days with it typically being from about 4 hours to about 20 days for obtaining MgAPSO crystals. The product is recovered by any convenient method such as centrifugation or filtration.

In synthesizing the MgAPSO compositions, it is preferred to employ reaction mixture compositions expressed in terms of the molar ratios as follows:

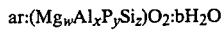

ar:$(Mg_wAl_xP_ySi_z)O_2$:b$H_2O$ wherein "R" is an organic templating agent; "a" is the amount of organic templating agent "R" and can have a value within the range of from zero (0) to about 6 and is more preferably an effective amount greater than zero to about 6; "b" has a value of from zero (0) to about 500, preferably between about 2 and about 300; and "w", "x", "y" and "z" represent the mole fractions of magnesium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| | Mole Fraction | | |
|---|---|---|---|
| Point | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total "w", "x", "y" and "z" such that (w+x+y+z)=1.00 mole. Molecular sieves containing magnesium, aluminum, phosphorus and silicon as framework tetrahedral oxides are prepared as follows:

Preparative Reagents

MgAPSO compositions are prepared using numerous reagents. Typical reagents which may be employed to prepare MgAPSOs include:

(a) Alipro: aluminum isopropoxide;
(b) CATAPAL: Trademark of Condea for hydrated pseudoboehmite;
(c) LUDOX-LS: Trademark of DuPont for an aqueous solution of 30 weight percent $SiO_2$ and 0.1 weight percent $Na_2O$;
(d) Mg(Ac)$_2$: magnesium acetate tetrahydrate, Mg($C_2H_3O_2$)$_2$·4$H_2O$;
(e) $H_3PO_4$: 85 weight percent aqueous phosphoric acid in water;
(f) TBAOH: tetraethylammonium hydroxide (40 wt. % in water);
(g) Pr$_2$NH: di-n-propylamine;
(h) Pr$_3$NH: tri-n-propylamine;
(i) Quin: Quinuclidine;
(j) MQuin: Methyl Quinuclidine hydroxide, (17.9% in water);
(k) C-hex: cyclohexylamine;
(l) TEAOH: tetraethylammonium hydroxide (40 wt. % in water);
(m) DEEA: Diethylethanolamine;
(n) i-Pr$_2$NH: di-isopropylamine;
(o) TEABr: tetraethylammonium bromide; and
(p) TPAOH: tetrapropylammonium hydroxide (40 wt. % in water).

Preparative Procedures

The MgAPSO compositions may be prepared by preparing reaction mixtures having a molar composition expressed as:

er:fMgO:h$Al_2O_3$:i$P_2O_5$:g$SiO_2$:j$H_2O$ wherein e, f, g, h, i and j represent the moles of template R, magnesium (expressed as the oxide, $SiO_2$, $Al_2O_3$, $P_2O_5$ ($H_3PO_4$ expressed as $P_2O_5$) and $H_2O$, respectively.

The reaction mixtures may be prepared by the following representative procedures, designated hereinafter as Methods A, B and C.

Method A

The reaction mixture is prepared by mixing the ground aluminum source (Alipro or CATAPAL) with the $H_3PO_4$ and water on a gradual basis with occasional cooling with an ice bath. The resulting mixture is blended until a homogeneous mixture is observed. When the aluminum source is CATAPAL the water and $H_3PO_4$ are first mixed with the CATAPAL added thereto. The magnesium acetate is dissolved in a portion of the water and is then added followed by addition of the LUDOX-LS. The combined mixture is blended until a homogenous mixture is observed. The organic templating agent is added to this mixture and blended until a homogenous mixture is observed. The resulting mixture (final reaction mixture) is placed in a lined (polytetrafluoroethylene) stainless steel pressure vessel and digested at a temperature (150° C. or 200° C.) for an effective time. Alternatively, if the digestion temperature is 100° C. the final reaction mixture is placed in a lined (polytetrafluoroethylene) screw top bottle for a time. Digestions are typically carried out under autogenous pressure. The products are removed from the reaction vessel, cooled and evaluated as set forth hereinafter.

Method B

When method B is employed the organic templating agent is di-n-propylamine. The aluminum source, silicon source and one-half of the water are first mixed and blended until a homogeneous mixture is observed. A second solution was prepared by mixing the remaining water, the H₃PO₄ and the magnesium acetate. This solution is then added to the above mixture. The magnesium acetate and H₃PO₄ solution is then added to the above mixture and blended until a homogeneous mixture is observed. The organic templating agent(s) is/are then added and the resulting reaction mixture digested and product recovered as in Method A.

Method C

Method C is carried out by mixing aluminum isopropoxide, LUDOX LS and water in a blender or by mixing water and aluminum iso-propoxide in a blender followed by addition of the LUDOX LS. H₃PO₄ and magnesium acetate are then added to this mixture. The organic templating agent is then added to the resulting mixture and digested and product recovered as in Method A.

MnAPSO MOLECULAR SIEVES

The MnAPSO molecular sieves of U.S. Ser. No. 600,175, filed Apr. 13, 1984 has a framework structure of $MnO_2^{-2}$, $AlO_2^-$, $PO_2^+$ and $SiO_2$ tetrahedral units having an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of the elements manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MnAPSO compositions are generally synthesized by hydrothermal crystallization from a reaction mixture containing reactive sources of manganese, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the MnAPSO product are obtained, usually a period of from several hours to several weeks. Typical effective times of from 2 hours to about 30 days, generally from about 4 hours to about 20 days, have been observed. The product is recovered by any convenient method such as centrifugation or filtration.

In synthesizing the MnAPSO compositions, it is preferred to employ a reaction mixture composition expressed in terms of the molar ratios as follows:

$$aR:(Mn_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of manganese, aluminum, phosphorus and silicon, respectively, and each has a value of at least 0.01.

In one embodiment of the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing manganese, aluminum, phosphorus and silicon as framework tetrahedral oxide units are prepared as follows:

Preparative Reagents

MnAPSO compositions may be prepared by using numerous reagents. Reagents which may be employed to prepare MnAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent SiO₂ and 0.1 weight percent Na₂O;
(d) H₃PO₄: 85 weight percent aqueous phosphoric acid;
(e) MnAc: Manganese acetate, $Mn(C_2H_3O_2)_2.4H_2O$;
(f) TEAOH: 40 weight percent aqueous solution of tetraethylammonium hydroxide;
(g) TBAOH: 40 weight percent aqueous solution of tetrabutylammonium hydroxide;
(h) Pr₂NH: di-n-propylamine, (C₃H₇)₂NH;
(i) Pr₃N: tri-n-propylamine, (C₃H₇)₃N;
(j) Quin: Quinuclidine, (C₇H₁₃N);
(k) MQuin: Methyl Quinuclidine hydroxide, (C₇H₁₃NCH₃OH);

(l) C-hex: cyclohexylamine;
(m) TMAOH: tetramethylammonium hydroxide;
(n) TPAOH: tetrapropylammonium hydroxide; and
(o) DEEA: 2-diethylaminoethanol.

Preparative Procedures

MnAPSOs are prepared by forming a starting reaction mixture by adding the H₃PO₄ to one half of the quantity of water. This mixture is mixed and to this mixture the aluminum isopropoxide or CATAPAL is added. This mixture is then blended until a homogeneous mixture is observed. To this mixture the LUDOX LS is added and the resulting mixture blended (about 2 minutes) until a homogeneous mixture is observed. A second mixture is prepared using the manganese acetate and the remainder (about 50%) of the water. The two mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

CoAPSO MOLECULAR SIEVES

The CoAPSO molecular sieves of U.S. Ser. No. 600,174, filed Apr. 13, 1984 have three-dimensional microporous framework structures of $CoO_2^-$, $AlO_2^-$, $PO_2^+$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y", and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

CoAPSO compositions are generally synthesized by hydrothermal crystallization from a reaction mixture containing reactive sources of cobalt, silicon, aluminum and phosphorus, an organic templating, i.e., structure-directing, agent, preferably a compound of an element of Group VA of the Periodic Table, and optionally an alkali metal. The reaction mixture is generally placed in a sealed pressure vessel, preferably lined with an inert plastic material such as polytetrafluoroethylene and heated, preferably under autogenous pressure at an effective temperature which is generally between 50° C. and 250° C. and preferably between 100° C. and 200° C. until crystals of the CoAPSO product are obtained, usually for an effective time of from several hours to several weeks. Generally the effective crystallization time will be from about 2 hours to about 30 days and typically from about 4 hours to about 20 days. The product is recovered by any convenient method such as centrifugation or filtration.

In synthesizing the CoAPSO, it is preferred to employ a reaction mixture composition expressed in terms of the molar ratios as follows:

$$aR:(Co_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; and "w", "x", "y" and "z" represent the mole fractions of cobalt, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing cobalt, aluminum, phosphorus and silicon as framework tetrahedral oxide units are prepared as follows:

Preparative Reagents

CoAPSO compositions may be prepared using numerous reagents. Reagents which may be employed to prepared CoAPSOs include:
(a) Alipro: aluminum isoproproxide;

(b) CATAPAL: Trademark of Condea Corporation for pseudoboehmite;
(c) LUDOX-LS: Trademark of DuPont for an aqueous solution of 30 weight percent $SiO_2$ and 0.1 weight percent $Na_2O$;
(d) $Co(Ac)_2$: cobalt acetate, $Co(C_2H_3O_2)_2.4H_2O$;
(e) $CoSO_4$: cobalt sulfate, $(CoSO_4.7H_2O)$;
(f) $H_3PO_4$: 85 weight percent phosphoric acid in water;
(g) TBAOH: tetrabutylammonium hydroxide (25 wt % in methanol);
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine $(C_7H_{13}N)$;
(k) MQuin: Methyl Quinuclidine hydroxide, $(C_7H_{13}NCH_3OH)$;
(l) C-hex: cyclohexylamine;
(m) TEAOH: tetraethylammonium hydroxide (40 wt. % in water);
(n) DEEA: diethanolamine;
(o) TPAOH: tetrapropylammonium hydroxide (40 wt. % in water); and
(p) TMAOH: tetramethylammonium hydroxide (40 wt. % in water).

Preparative Procedure

CoAPSO compositions may be prepared by preparing reaction mixtures having a molar composition expressed as:

$$eR:fCoO:hAl_2O_3:iP_2O_5:gSiO_2:jH_2O$$

wherein e, f, h, i, g and j represent the moles of template R, cobalt (expressed as the oxide), $Al_2O_3$, $P_2O_5$ ($H_3PO_4$ expressed as $P_2O_5$), $SiO_2$ and $H_2O$, respectively.

The reaction mixtures are prepared by forming a starting reaction mixture comprising the $H_3PO_4$ and one half of the water. This mixture is stirred and the aluminum source (Alipro or CATAPAL) added. The resulting mixture is blended until a homogeneous mixture is observed. The LUDOX-LS is then added to the resulting mixture and the new mixture blended until a homogeneous mixture is observed. The cobalt source (e.g., $Co(Ac)_2$, $Co(SO_4)$ or mixtures thereof) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at a temperature (150° C., 200° C. or 225° C.) for a time. Digestions are typically carried out at the autogenous pressure. The products are removed from the reaction vessel and cooled.

ZnAPSO MOLECULAR SIEVES

The ZnAPSO molecular sieves of U.S. Ser. No. 600,170, filed Apr. 13, 1984 comprise framework structures of $ZnO_2^{-2}$, $AlO_2^-$, $PO_2^+$ and $SiO_2$ tetrahedral units having an empirical chemical composition on an anhydrous basis expressed by the formula:

$$mR:(Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

ZnAPSO compositions are generally synthesized by hydrothermal crystallization at effective process conditions from a reaction mixture containing active sources of zinc, silicon, aluminum and phosphorus, preferably an organic templating, i.e., structure-directing, agent, preferably a compound of an element or Group VA of the Periodic Table, and/or optionally an alkali of other metal. The reaction mixture is generally placed in a sealed pressure vessel, preferably lined with an inert plastic material such as polytetrafluoroethylene and heated, preferably under autogenous pressure, at a temperature between 50° C. and 250° C., and preferably between 100° C. and 200° C. until crystals of the ZnAPSO product are obtained, usually a period of from several hours to several weeks. Generally the effective crystallization period is from about 2 hours to about 30 days with typical periods of from about 4 hours to about 20 days being employed to obtain ZnAPSO products. The product is recovered by any convenient method such as centrifugation or filtration.

In synthesizing the ZnAPSO compositions, it is preferred to employ a reaction mixture composition expressed in terms of the molar ratios as follows:

$$aR:(Zn_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, more preferably between about 2 and about 300; and "w", "x", "y" and "z" represent the mole fractions of zinc, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing zinc, aluminum, phosphorus and silicon as framework tetrahedral oxide units are prepared as follows:

Preparative Reagents

ZnAPSO compositions are typically prepared using numerous reagents. Reagents which may be employed to prepare ZnAPSOs include:

(a) Alipro: aluminum isopropoxide;
(b) LUDOX-LS: LUDOX-LS is the trade name of DuPont for an aqueous solution of 30 weight percent $SiO_2$ and 0.1 weight percent $Na_2O$;
(c) CATAPAL: Trademark of Condea Corporation for hydrated pseudoboehmite;
(d) $H_3PO_4$: 85 weight percent aqueous phosphoric acid;
(e) ZnAc: Zinc Acetate, $Zn(C_2H_3O_2)_2 \cdot 4H_2O$;
(f) TEAOH: 40 weight percent aqueous solution of tetraethylammonium hydroxide;
(g) TBAOH: 40 weight percent aqueous solution of tetrabutylammonium hydroxide;
(h) TMAOH: Tetramethylammonium hydroxide pentahydrate, $(CH_3)_4NOH \cdot 5H_2O$;
(i) TPAOH: 40 weight percent aqueous solution of tetrapropylammonium hydroxide, $(C_3H_7)_4NOH$;
(j) $Pr_2NH$: di-n-propylamine, $(C_3H_7)_2NH$;
(k) $Pr_3N$: Tri-n-propylamine, $(C_3H_7)_3N$;
(l) Quin: Quinuclidine, $(C_7H_{13}N)$;
(m) C-hex: cyclohexylamine; and
(n) DEEA: diethylethanolamine, $(C_2H_5)_2NC_2H_5OH$.

Preparative Procedure

ZnAPSO compositions are typically prepared by forming reaction mixtures having a molar composition expressed as:

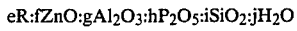

$eR : fZnO : gAl_2O_3 : hP_2O_5 : iSiO_2 : jH_2O$ wherein e, f, g, h, i and j represent the moles of template R, zinc (expressed as the oxide), $Al_2O_3$, $P_2O_5$ ($H_3PO_4$ expressed as $P_2O_5$), $SiO_2$ and $H_2O$, respectively.

The reaction mixtures are generally prepared by forming a starting reaction mixture comprising the $H_3PO_4$ and a portion of the water. This mixture is stirred and the aluminum source added. The resulting mixture is blended until a homogeneous mixture is observed. The LUDOX LS is then added to the resulting mixture and the new mixture blended until a homogeneous mixture is observed. The zinc source (zinc acetate) is dissolved in the remaining water and combined with the first mixture. The combined mixture is blended until a homogenous mixture is observed. The organic templating agent is added to this mixture and blended for about two to four minutes until a homogenous mixture is observed. The resulting mixture (final reaction mixture) is placed in a lined (polytetrafluoroethylene) stainless steel pressure vessel and digested at an effective temperature for an effective time. Digestions are typically carried out under autogenous pressure. The products are removed from the reaction vessel and cooled.

FeAPSO MOLECULAR SIEVES

The FeAPSO molecular sieves of U.S. Ser. No. 600,173, filed Apr. 13, 1984 have molecular sieves having a three-dimensional microporous crystal framework structures of $FeO_2^{-2}$, (and/or $FeO_2^{-}$), $AlO_2^{-}$, $PO_2^{+}$ and $SiO_2$ tetrahedral oxide units and having a unit empirical formula, on an anhydrous basis, of:

$$mR : (Fe_wAl_xP_ySi_z)O_2 \qquad (1)$$

wherein "R" represents at least one organic templating agent present in the intracrystalline pore system; "m" represents the moles of "R" present per mole of $(Fe_wAl_xP_ySi_z)O_2$ and has a value of from zero (0) to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

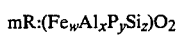

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The FeAPSOs of the instant invention are generally synthesized by hydrothermal crystallization from a reaction mixture comprising reactive sources of iron, aluminum, phosphorus and silicon, and preferably one or more organic templating agents. Optionally, alkali or other metal(s) may be present in the reaction mixture and may act as templating agents. The reaction mixture is generally placed in a pressure vessel, preferably lined with an inert plastic material, such as polytetrafluoroethylene, and heated, preferably under autogenous pressure, at an effective temperature which is generally between about 50° C. and about 250° C., and preferably between about 100° C. and 200° C., until crystals of the FeAPSO product are obtained, usually a period of from several hours to several weeks. Molecular sieves containing iron, aluminum, phosphorus and silicon as framework tetrahedral oxide units are typically prepared as follows:

Preparative Reagents

FeAPSO compositions may be prepared using numerous reagents. Reagents which may employed to prepare FeAPSOs include:
(a) Alipro: aluminum isopropoxide, Al(OCH(CH$_3$)$_2$)$_3$;
(b) LUDOX-LS: LUDOX-LS is the trademark of DuPont for an aqueous solution of 30 weight percent SiO$_2$ and 0.1 weight percent Na$_2$O;
(c) CATAPAL: trademark for hydrated aluminum oxide containing about 75 wt. percent Al$_2$O$_3$ (pseudoboehmite phase) and about 25 wt. percent water;
(d) Fe(Ac)$_2$: Iron (II) acetate;
(e) FeSO$_4$: Iron (II) sulfate hexahydrate;
(f) H$_3$PO$_4$: 85 weight percent phosphoric acid in water;
(g) TEAOH: 40 weight percent aqueous solution of tetraethylammonium hydroxide;
(h) TBAOH: 40 weight percent aqueous solution of tetrabutylammonium hydroxide;
(i) Pr$_2$NH: di-n-propylamine ((C$_3$H$_7$)$_2$NH);
(j) Pr$_3$N: tri-n-propylamine ((C$_3$H$_7$)$_3$N);
(k) Quin: Quinuclidine (C$_7$H$_{13}$N);
(l) MQuin: Methyl Quinuclidine hydroxide (C$_7$H$_{13}$NCH$_3$OH);
(m) TMAOH: tetramethylammonium hydroxide pentahydrate; and
(o) C-hex: cyclohexylamine.

(a) Reaction mixtures to prepare FeAPSOs are typically prepared by grinding an aluminum isopropoxide in a blender followed by slowly adding a H$_3$PO$_4$ solution with mixing. A solution/dispersion of iron acetate in water is added and then a silica (e.g., LUDOX-LS) is added. The organic templating agent is then added to this mixture, or in some cases one-half of this mixture, and the mixture blended to form a homogeneous mixture. For example, in one embodiment, the number of moles of each component in the reaction mixture is as follows:

| Component | Moles |
|---|---|
| Al$_2$O$_3$ | 0.9 |
| P$_2$O$_5$ | 0.9 |
| SiO$_2$ | 0.2** |
| FeO* | 0.2 |
| TEAOH | 1.0 |
| H$_2$O | 50 |

*Iron (II) acetate reported as Iron (II) oxide.
**SiO$_2$ was 0.6 in examples 5C to 8C The reaction mixture is sealed in a stainless steel pressure vessel lined with polytetrafluoroethylene and heated in an oven at a temperature, time and under autogenous pressure. The solid reaction product is recovered by filtration, washed with water and dried at room temperature.

(b) In another embodiment, reaction mixtures are prepared by grinding the aluminum isopropoxide in a blender followed by addition of a solution/dispersion of iron(II) acetate. H$_3$PO$_4$ is added to this mixture and the resulting mixture blended to form a homogeneous mixture. A silica (e.g., LUDOX-LS) is added to this mixture except that in some instances the silica may be added with the H$_3$PO$_4$. The resulting mixtures were blended until a homogeneous mixture is observed. Organic templating agent is added to each mixture and the resulting mixtures placed in a stainless steel pressure vessel lined with polytetrafluoroethylene and heated, washed and the product recovered. In this embodiment the number of moles of each component in the reaction mixture is as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| Template | 1.0 |
| H$_2$O | 50 |

*Iron (II) acetate reported as Iron (II) oxide.

CoMnAPSO MOLECULAR SIEVES

CoMnAPSO molecular sieves may be expressed by the empirical chemical formula (anhydrous) as follows:

$$mR:(Co_uMn_vAl_xP_ySi_z)O_2$$

where "u", "v", "x", "y" and "z" represent the mole fractions of cobalt, manganese, aluminum, phosphorus and silicon respectively. The CoMnAPSO molecular sieves have an empirical chemical composition on an anhydrous basis expressed by the formula:

$$mR:(Co_uMn_vAl_xP_ySi_z)O_2$$

wherein "R" represents at least one organic templating agent present in the intracrystalline pore system; "m" represents the molar amount of "R" present per mole of (Co$_u$Mn$_v$Al$_x$P$_y$Si$_z$)O$_2$ from zero (0) to about 0.3; and "u", "v", "x", "y" and "z" represent the mole fractions of cobalt, manganese, aluminum, phosphorus and silicon, respectively, present as tetrahedral oxides. The mole fractions "u", "v", "x", "y", and "z" are generally defined as being within the limiting compositional values or points as follows, wherein "w", the combined mole fractions of manganese and cobalt, is the sum of "u" and "v":

| Point | Mole Fraction | | |
|---|---|---|---|
| | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

Preferably the mole fractions u, v, x, y and z will fall within the limiting compositional values or points as follows:

| Point | Mole Fraction | | |
|---|---|---|---|
| | x | y | (z + w) |
| a | 0.55 | 0.42 | 0.03 |
| b | 0.42 | 0.55 | 0.03 |
| c | 0.10 | 0.55 | 0.35 |
| d | 0.55 | 0.10 | 0.35 |

CoMnAPSO compositions are generally synthesized by hydrothermal crystallization from a reaction mixture containing reactive sources of cobalt, manganese, aluminum, phosphorus and silicon and preferably an organic templating agent, i.e., structure-directing, agent. The structure-directing agents are preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure and at typical effective temperatures between 50° C. and 250° C., preferably between 100° C. and 200° C., until crystals of the CoMnAPSO product are obtained, usually over a period of from several hours to several weeks. Typical effective crystallization times are from about 2 hours to 30 days with from about 4 hours to about 20 days being generally employed to obtain CoMnAPSO products. The product is received by any convenient method such as centrifugation or filtration.

In synthesizing the CoMnAPSO compositions, it is preferred to employ a reaction mixture composition expressed in terms of the molar ratios as follows:

$aR:(Co_uMn_vAl_xP_ySi_z)O_2:bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "u", "v", "x", "y", and "z" represent the mole freactions of elements cobalt, manganese, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.37 | 0.03 |
| G | 0.37 | 0.60 | 0.03 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "u", "v", "x", "y" and "z" such that (u+v+x+y+z)=1.00 mole. CoMnAPSO compositions were prepared using numerous regents.

Reagents which may be employed to prepare CoMnAPSOs include:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: 85 weight percent phosphoric acid;
(d) MnAc: Manganese acetate, $Mn(C_2H_3O_2)_2.4H_2O$;
(e) CoAc: Cobalt Acetate, $Co(C_2H_3O_2)_2.4H_2O$;
(f) TEAOH: 40 weight percent aqueous solution of tetraethylammonium hydroxide; and
(g) $Pr_2NH$: di-n-propylamine, $(C_3H_7)_2NH$.

Preparative Procedures

CoMnAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed. A second mixture is prepared using manganese acetate and one half of the remaining water. A third mixture is prepared using cobalt acetate and one half of the remaining water. The three mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. The pH of the mixture is measured and adjusted for temperature. The mixture is then placed in a lined (polytetrafluoroethylene) stainless steel pressure vessel and digested at an effective temperature for an effective time. Digestions are typically carried out under autogenous pressure.

CoMnMgAPSO MOLECULAR SIEVES

The CoMnMgAPSO molecular sieves of U.S. Ser. No. 600,182, filed Apr. 13, 1984 have three-dimensional microporous framework structures of $CoO_2^{-2}$, $MnO_2^{-2}$, $MgO_2^{-2}$, $AlO_2^-$, $PO_2^+$ and $SiO_2$ tetrahedral oxide units and have an empirical chemical composition on an anhydrous basis expressed by the formula:

$mR:(Co_tMn_uMg_vAl_xP_ySi_z)O_2$ wherein "R" represents at least one organic templating agent present in the intracrystalline pore system; "m" represents the molar amount of "R" present per mole of $(Co_tMn_uMg_vAl_xP_ySi_z)O_2$, and has a value of from zero to about 0.3; and "t", "u", "v", "x", "y" and "z" represent the mole fractions of cobalt, manganese, magnesium, aluminum, phosphorus and silicon, respectively, present as tetrahedral oxides, each having a value of at least 0.01. The mole fractions "t", "u", "v", "x", "y" and "z" are generally defined as being within the limiting compositional values or points as follows, wherein "w", the combined mole fractions of cobalt, manganese and magnesium, is the sum of "t", "u", and "v":

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the CoMnMgAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.41 | 0.04 |
| b | 0.41 | 0.55 | 0.04 |
| c | 0.10 | 0.55 | 0.35 |
| d | 0.55 | 0.10 | 0.35 |

CoMnMgAPSO compositions are generally synthesized by hydrothermal crystallization from a reaction mixture containing reactive sources of cobalt, manganese, magnesium, aluminum, phosphorus and silicon, and preferably an organic templating agent, i.e., structure-directing, agent. The structure-directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the CoMnMgAPSO product are obtained, usually over a period of from several hours to several weeks. Typical crystallization times are from about 2 hours to about 30 days with from about 4 hours to about 20 days generally being employed to obtain CoMnMgAPSO products. The product is recovered by any convenient method such as centrifugation or filtration.

In synthesizing the CoMnMgAPSO compositions, it is preferred to employ a reaction mixture composition expressed in terms of the molar ratios as follows:

$$aR:(Co_tMn_uMg_vAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "t", "u", "v", "x", "y", and "z" represent the mole fractions of cobalt, manganese, magnesium, aluminum, phosphorus and silicon, respectively, and each has a value of at least 0.01.

In a preferred embodiment the reaction mixture is selected such that the mole fractions "w", "x", "y" and "z", where "w" is the sum of "t"+"u"+"v", are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "t", "u", "v", "x", "y" and "z" such that (t+u+v+x+y+z)=1.00 mole. Molecular sieves containing cobalt, manganese, magnesium, aluminum, phosphorus and silicon as framework tetrahedral oxide units are prepared as follows:

Preparative Reagents

CoMnMgAPSO compositions may be prepared by using numerous reagents. Reagents which may be employed to prepare CoMnAPSOs include:
 (a) Alipro: aluminum isopropoxide;
 (b) LUDOX-LS: LUDOX-LS is the tradename of DuPont for an aqueous solution of 30 weight percent $SiO_2$ and 0.1 weight percent $Na_2O$;
 (c) $H_3PO_4$: aqueous solution which is 85 weight percent phosphoric acid;
 (d) MnAc: Manganese acetate, $Mn(C_2H_3O_2)_2 \cdot 4H_2O$;
 (e) CoAc: Cobalt Acetate, $Co(C_2H_3O_2)_2 \cdot 4H_2O$;
 (f) MgAc: Magnesium Acetate $Mg(C_2H_3O_2) \cdot 4H_2O$;
 (g) TEAOH: 40 weight percent aqueous solution of tetraethylammonium hydroxide; and
 (h) $Pr_2NH$: di-n-propylamine, $(C_3H_7)_2NH$.

Preparative Procedures

CoMnMgAPSOs may be prepared by forming a starting reaction mixture by adding $H_3PO_4$ and one half of the quantity of water. To this mixture an aluminum isoproxide is added. This mixture is then blended until a homogeneous mixture is observed. To this mixture a silica (e.g., LUDOX-LS) is added and the resulting mixture blended (about 2 minutes) until a homogeneous mixture is observed.

Three additional mixtures are prepared using cobalt acetate, magnesium acetate and manganese acetate mixture. The four mixtures are then admixed and the resulting mixture blended until a homogeneous mixture is observed. An organic templating agent is then added to the resulting mixture and the resulting mixture blended until a homogeneous mixture is observed, i.e., about 2 to 4 minutes. The mixture is then placed in a lined (polytetrafluoroethylene) stainless steel pressure vessel and digested at a temperature for a time. Digestions are typically carried out under autogenous pressure.

AsAPSO MOLECULAR SIEVES

The AsAPSO molecular sieves of U.S. Ser. No. 599,808, filed Apr. 13, 1984, and U.S. Ser. No. 845,484 filed Mar. 31, 1986 have a framework structure of $AsO_2^n$, $AlO_2^-$, $PO_2^+$ and $SiO_2$ tetrahedral units having an empirical chemical composition on an anhydrous basis expressed by the formula:

$$mR:(As_wAl_xP_ySi_z)O_2$$

wherein "R" represents at least one organic templating agent present in the intracrystalline pore system; "m" represents the molar amount of "R" present per mole of $(As_wAl_xP_ySi_z)O_2$ and has a value of zero to about 0.3, but is preferably not greater than 0.15; and "w", "x", "y" and "z" represent the mole fractions of the elements arsenic, aluminum, phosphorus and silicon, respectively, present as tetrahedral oxides. The mole fractions "w", "x", "y" and "y" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the AsAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |

-continued

| | Mole Fraction | | |
|---|---|---|---|
| Point | x | y | (z + w) |
| f | 0.60 | 0.01 | 0.39 |

In an especially preferred subclass of the AsAPSO molecular sieves, the values of w, x, y and z are as follows:

| | Mole Fraction | | |
|---|---|---|---|
| Point | x | y | (z + w) |
| g | 0.50 | 0.40 | 0.10 |
| h | 0.42 | 0.48 | 0.10 |
| i | 0.38 | 0.48 | 0.14 |
| j | 0.38 | 0.37 | 0.25 |
| k | 0.45 | 0.30 | 0.25 |
| l | 0.50 | 0.30 | 0.20 |

AsAPSO compositions are generally synthesized by hydrothermal crystallization from a reaction mixture containing reactive sources of arsenic, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the AsAPSO product are obtained, usually a period of from several hours to several weeks. Typical effective times of from 2 hours to about 30 days, generally from about 12 hours to about 10 days, have been observed. The product is recovered by any convenient method such as centrifugation or filtration.

In synthesizing the AsAPSO compositions, it is preferred to employ a reaction mixture composition expressed in terms of the molar ratios as follows:

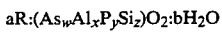

$$aR:(As_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably not greater than about 60; and "w", "x", "y" and "z" represent the mole fractions of arsenic, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| | Mole Fraction | | |
|---|---|---|---|
| Point | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |

| | Mole Fraction | | |
|---|---|---|---|
| Point | x | y | (z + w) |
| J | 0.60 | 0.01 | 0.39 |

Especially preferred reaction mixtures are those containing from about 1 to about 2 total moles of silicon and arsenic, and from about 1 to about 2 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing arsenic, aluminum, phosphorus and silicon as framework tetrahedral oxide units are prepared as follows:

Preparative Reagents

AsAPSO compositions may be prepared by using numerous reagents. Reagents which may be employed to prepare AsAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) $As_2O_5$, arsenic(V) oxide;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

AsAPSOs may be prepared by forming a starting reaction mixture by dissolving the arsenic(V) oxide and the $H_3PO_4$ in at least part of the water. To this solution the aluminum isopropoxide or CATAPAL is added. This mixture is then blended until a homogeneous mixture is observed. To this mixture the templating agent and then the silica is added and the resulting mixture blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BAPSO MOLECULAR SIEVES

The BAPSO molecular sieves of U.S. Ser. No. 600,177, filed Apr. 13, 1984, and U.S. Ser. No. 845,255 filed Mar. 28, 1986 have a framework structure of $BO_2^-$, $AlO_2^-$, $PO_2^+$ and $SiO_2$ tetrahedral units having an empirical chemical composition on an anhydrous basis expressed by the formula:

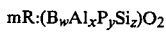

$$mR:(B_wAl_xP_ySi_z)O_2$$

wherein "R" represents at least one organic templating agent present in the intracrystalline pore system; "m" represents the molar amount of "R" present per mole of $(B_wAl_xP_ySi_z)O_2$ and has a value of zero to about 0.3, but is preferably not greater than 0.15; and "w", "x", "y" and "z" represent the mole fractions of the elements boron, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the BAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the BAPSO molecular sieves, the values of w, x, y and z are as follows:

| Point | Mole Fraction | | |
|---|---|---|---|
| | x | y | (z + w) |
| g | 0.51 | 0.42 | 0.07 |
| h | 0.45 | 0.48 | 0.07 |
| i | 0.33 | 0.48 | 0.19 |
| j | 0.33 | 0.38 | 0.29 |
| k | 0.36 | 0.35 | 0.29 |
| l | 0.51 | 0.35 | 0.14 |

BAPSO compositions are generally synthesized by hydrothermal crystallization from a reaction mixture containing reactive sources of boron, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BAPSO product are obtained, usually a period of from several hours to several weeks. Typical effective times of from 2 hours to about 30 days, generally from about 4 hours to about 20 days, have been observed. The product is recovered by any convenient method such as centrifugation or filtration.

In synthesizing the BAPSO compositions, it is preferred to employ a reaction mixture composition expressed in terms of the molar ratios as follows:

$$aR:(B_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "w", "x", "y" and "z" represent the mole fractions of boron, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 1.0 to about 2 total moles of silicon and boron, and from about 0.75 to about 1.25 moles of aluminum, per mole of phosphorus.

In the foregoing expression of the reaction composition, the reactants are normalized with respect to the total of "w", "x", "y" and "z" such that $(w+x+y+z)=1.00$ mole. Molecular sieves containing boron, aluminum, phosphorus and silicon as framework tetrahedral oxide units are prepared as follows:

Preparative Reagents

BAPSO compositions may be prepared by using numerous reagents. Reagents which may be employed to prepare BAPSOs include:

(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) $H_3BO_3$, boric acid, and trialkyl borates;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;

(n) TPAOH: tetrapropylammonium hydroxide; and
(o) DEEA: 2-diethylaminoethanol;
(p) Tetraalkylorthosilicates, such as tetraethylorthosilicate.

Preparative Procedures

BAPSOs may be prepared by forming a starting reaction mixture by dissolving aluminum isopropoxide in an alcohol such as isopropanol, adding the $H_3PO_4$ and recovering the solid which precipitates. This solid is then added to water, and trialkylborate (for example trimethyl borate added, followed by silica and the templating agent. This mixture is then blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BeAPSO MOLECULAR SIEVES

The BeAPSO molecular sieves of U.S. Ser. No. 600,176, filed Apr. 13, 1984, and U.S. Ser. No. 841,752 filed Mar. 20, 1986 have a framework structure of $BeO_2^{-2}$, $AlO_2^{-}$, $PO_2^{+}$ and $SiO_2$ tetrahedral units having an empirical chemical composition on an anhydrous basis expressed by the formula:

$$mR:(Be_wAl_xP_ySi_z)O_2$$

wherein "R" represents at least one organic templating agent present in the intracrystalline pore system; "m" represents the molar amount of "R" present per mole of $(Be_wAl_xP_ySi_z)O_2$ and has a value of zero to about 0.3, but is preferably not greater than 0.15; and "w", "x", "y" and "z" represent the mole fractions of the elements beryllium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the BeAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

BeAPSO compositions are generally synthesized by hydrothermal crystallization from a reaction mixture containing reactive sources of beryllium, silicon, aluminum and phosphorus, preferably an organic templating, i.e., structure-directing, agent, preferably a compound of an element of Group VA of the Periodic Table, and-/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the BeAPSO product are obtained, usually a period of from several hours to several weeks. Typical effective times of from 2 hours to about 30 days, generally from about 4 hours to about 20 days, have been observed, with from 1 to 10 days being preferred. The product is recovered by any convenient method such as centrifugation or filtration.

In synthesizing the BeAPSO compositions, it is preferred to employ a reaction mixture composition expressed in terms of the molar ratios as follows:

$$aR:(Be_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "w", "x", "y" and "z" represent the mole fractions of beryllium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing beryllium, aluminum, phosphorus and silicon as framework tetrahedral oxide units are prepared as follows:

Preparative Reagents

BeAPSO compositions may be prepared by using numerous reagents. Reagents which may be employed to prepare BeAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) beryllium sulfate, $BeSO_4$;
(f) TEAOH: 40 weight percent aqueous solution of tetraethylammonium hydroxide;
(g) TBAOH: 40 weight percent aqueous solution of tetrabutylammonium hydroxide;

(h) Pr₂NH: di-n-propylamine, (C₃H₇)₂NH;
(i) Pr₃N: tri-n-propylamine, (C₃H₇)₃N;
(j) Quin: Quinuclidine, (C₇H₁₃N);
(k) MQuin: Methyl Quinuclidine hydroxide, (C₇H₁₃NCH₃OH);
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

BeAPSOs may be prepared by forming a starting solution by mixing H₃PO₄ in at least part of the water. To this solution is added beryllium sulfate (or another beryllium salt) and the resultant mixture stirred until a homogeneous solution is obtained. To this solution may be added successively the aluminum oxide, the silica and the templating agent, with the mixture being stirred between each addition until it is homogeneous. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

CAPSO MOLECULAR SIEVES

The CAPSO molecular sieves of U.S. Ser. No. 599,830, filed Apr. 13, 1984, and U.S. Ser. No. 852,174 filed Apr. 15, 1986 have a framework structure of $CrO_2^n$, $AlO_2^-$, $PO_2^+$ and $SiO_2$ tetrahedral units (where "n" is $-1$, 0 or $+1$) having an empirical chemical composition on an anhydrous basis expressed by the formula:

$$mR:(Cr_wAl_xP_ySi_z)O_2$$

wherein "R" represents at least one organic templating agent present in the intracrystalline pore system; "m" represents the molar amount of "R" present per mole of $(Cr_wAl_xP_ySi_z)O_2$ and has a value of zero to about 0.3, but is preferably not greater than 0.15; and "w", "x", "y" and "z" represent the mole fractions of the elements chromium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the CAPSO molecular sieves, the values of x and y in the above formula are each within the range of about 0.4 to 0.5 and (z+w) is in the range of about 0.02 to 0.15.

Since the exact nature of the CAPSO molecular sieves is not clearly understood at present, although all are believed to contain $CrO_2$ tetrahedra in the three-dimensional microporous crystal framework structure, it is advantageous to characterize the CAPSO molecular sieves by means of their chemical composition. This is due to the low level of chromium present in certain of the CAPO molecular sieves prepared to date which makes it difficult to ascertain the exact nature of the interaction between chromium, aluminum, phosphorus and silicon. As a result, although it is believed that $CrO_2$ tetrahedra are substituted isomorphously for $AlO_2$, $PO_2$ or $SiO_2$ tetrahedra, it is appropriate to characterize certain CAPSO compositions by reference to their chemical composition in terms of the mole ratios of oxides.

CAPSO compositions are generally synthesized by hydrothermal crystallization from a reaction mixture containing reactive sources of chromium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the CAPSO product are obtained, usually a period of from several hours to several weeks. Typical effective times of from 2 hours to about 30 days, generally from about 4 hours to about 20 days, and preferably about 1 to about 10 days, have been observed. The product is recovered by any convenient method such as centrifugation or filtration.

In synthesizing the CAPSO compositions, it is preferred to employ a reaction mixture composition expressed in terms of the molar ratios as follows:

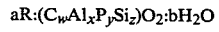

$$aR:(Cr_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "w", "x", "y" and "z" represent the mole fractions of chromium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 0.3 to about 0.5 total moles of silicon and chromium, and from about 0.75 to about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing chromium, aluminum, phosphorus and silicon as framework tetrahedral oxide units are prepared as follows:

Preparative Reagents

CAPSO compositions may be prepared by using numerous reagents. Reagents which may be employed to prepare MnAPSOs include:

(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) chromium acetate, and chromium acetate hydroxide;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

CAPSOs may be prepared by forming a starting solution by dissolving $H_3PO_4$ in at least part of the water. To this solution the aluminum isopropoxide is added. This mixture is then blended until a homogeneous mixture is observed. To this mixture the silica, the chromium acetate or chromium acetate hydroxide and the templating agent are successively added and at each step the resulting mixture is blended until a homogeneous mixture is observed.

Alternatively, the water and aluminum isopropoxide may first be mixed, and then the silica, the chromium acetate or chromium acetate hydroxide, the phosphoric acid and the templating agent added, and again at each step the resulting mixture is blended until a homogeneous mixture is observed.

In either case, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GaAPSO MOLECULAR SIEVES

The GaAPSO molecular sieves of U.S. Ser. No. 599,925, filed Apr. 13, 1984, and U.S. Ser. No. 845,985 filed Mar. 31, 1986 have a framework structure of $GaO_2^-$, $AlO_2^-$, $PO_2^+$ and $SiO_2$ tetrahedral units having an empirical chemical composition on an anhydrous basis expressed by the formula:

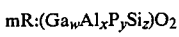

$$mR:(Ga_wAl_xP_ySi_z)O_2$$

wherein "R" represents at least one organic templating agent present in the intracrystalline pore system; "m" represents the molar amount of "R" present per mole of $(Ga_wAl_xP_ySi_z)O_2$ and has a value of zero to about 0.3, but is preferably not greater than 0.2; and "w", "x", "y" and "z" represent the mole fractions of the elements gallium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the GaAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the GaAPSO molecular sieves, the values of w, x, y and z are as follows:

| Point | Mole Fraction | | |
|---|---|---|---|
| | x | y | (z + w) |
| g | 0.45 | 0.40 | 0.15 |
| h | 0.33 | 0.52 | 0.15 |
| i | 0.20 | 0.52 | 0.28 |
| j | 0.20 | 0.45 | 0.35 |
| k | 0.36 | 0.29 | 0.35 |
| l | 0.45 | 0.29 | 0.26 |

GaAPSO composition are generally synthesized by hydrothermal crystallization from a reaction mixture containing reactive sources of gallium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GaAPSO product are obtained, usually a period of from several hours to several weeks. Typical effective times of from 2 hours to about 30 days, generally from about 4 hours to about 20 days, and preferably about 2 to about 15 days, have been observed. The product is recovered by any convenient method such as centrifugation or filtration.

In synthesizing the GaAPSO compositions, it is preferred to employ a reaction mixture composition expressed in terms of the molar ratios as follows:

$$aR:(Ga_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably not greater than about 20; and "w", "x", "y" and "z" represent the mole fractions of gallium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

|       | Mole Fraction |      |         |
|-------|---------------|------|---------|
| Point | x             | y    | (z + w) |
| F     | 0.60          | 0.38 | 0.02    |
| G     | 0.38          | 0.60 | 0.02    |
| H     | 0.01          | 0.60 | 0.39    |
| I     | 0.01          | 0.01 | 0.98    |
| J     | 0.60          | 0.01 | 0.39    |

Especially preferred reaction mixtures are those containing from about 0.5 to about 1.0 total moles of silicon and gallium, and from about 0.75 about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing gallium, aluminum, phosphorus and silicon as framework tetrahedral oxide units are prepared as follows:

Preparative Reagents

GaAPSO compositions may be prepared by using numerous reagents. Reagents which may be employed to prepare GaAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) gallium hydroxide, or gallium sulfate;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

GaAPSOs may be prepared by forming a starting solution by dissolving the $H_3PO_4$ in at least part of the water. To this solution the aluminum hydroxide or isopropoxide is added. This mixture is then blended until a homogeneous mixture is observed. To this mixture is added a second solution prepared by adding silica to a solution containing the gallium hydroxide and the templating agent and then the combined mixture is blended until a homogeneous mixture is observed.

Alternatively, the templating agent may be added to the solution containing the phosphoric acid abd water, and a solution of gallium sulfate in water added, followed by successive additions of silica and aluminum oxide and then the combined mixture is blended until a homogeneous mixture is observed.

In either case, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GeAPSO MOLECULAR SIEVES

The GeAPSO molecular sieves of U.S. Ser. No. 599,971, filed Apr. 13, 1984, and U.S. Ser. No. 852,175 filed Apr. 15, 1986 have a framework structure of $GeO_2$, $AlO_2^-$, $PO_2^+$ and $SiO_2$ tetrahedral units having an empirical chemical composition on an anhydrous basis expressed by the formula:

$$mR:(Ge_wAl_xP_ySi_z)O_2$$

wherein "R" represents at least one organic templating agent present in the intracrystalline pore system; "m" represents the molar amount of "R" present per mole of $(Ge_wAl_xP_ySi_z)O_2$ and has a value of zero to about 0.3, but is preferably not greater than 0.15; and "w", "x", "y" and "z" represent the mole fractions of the elements germanium, aluminum, phosphorus and silicon, respectively, present as tetrahedral oxides. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the GeAPSO molecular sieves, the values of w, x, y and z are as follows:

| | Mole Fraction | | |
|---|---|---|---|
| Point | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the GeAPSO molecular sieves, the values of w, x, y and z are as follows:

| | Mole Fraction | | |
|---|---|---|---|
| Point | x | y | (z + w) |
| g | 0.60 | 0.35 | 0.05 |
| h | 0.47 | 0.48 | 0.05 |
| i | 0.40 | 0.48 | 0.12 |
| j | 0.40 | 0.36 | 0.24 |
| k | 0.46 | 0.30 | 0.24 |
| l | 0.60 | 0.30 | 0.10 |

GeAPSO compositions are generally synthesized by hydrothermal crystallization from a reaction mixture containing reactive sources of germanium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the GeAPSO product are obtained, usually a period of from several hours to several weeks. Typical effective times of from 2 hours to about 30 days, generally from about 4 hours to about 20 days, and preferably about 12 hours to about 7 days have been observed. The product is recovered by any convenient method such as centrifugation or filtration.

In synthesizing the GeAPSO compositions, it is preferred to employ a reaction mixture composition expressed in terms of the molar ratios as follows:

aR:(Ge$_w$Al$_x$P$_y$Si$_z$)O$_2$:bH$_2$O wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20, and desirably not greater than about 10; and "w", "x", "y" and "z" represent the mole fractions of germanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| | Mole Fraction | | |
|---|---|---|---|
| Point | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 0.2 to about 0.3 total moles of silicon and germanium, and from about 0.75 to about 1.25 moles of aluminum, per mole of phosphorus.

In the foregoing expression of the reaction composition, the reactants are normalized with respect to the total "w", "x", "y" and "z" such that (w+x+y+z)=1.00 mole. Molecular sieves containing germanium, aluminum, phosphorus and silicon as framework tetrahedral oxide units are prepared as follows:

Preparative Reagents

GeAPSO compositions may be prepared by using numerous reagents. Reagents which may be employed to prepare GeAPSOs include:

(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent SiO$_2$ and 0.1 weight percent Na$_2$O;
(d) H$_3$PO$_4$: 85 weight percent aqueous phosphoric acid;
(e) germanium tetrachloride or germanium ethoxide;
(f) TEAOH: 40 weight percent aqueous solution of tetraethylammonium hydroxide;
(g) TBAOH: 40 weight percent aqueous solution of tetrabutylammonium hydroxide;
(h) Pr$_2$NH: di-n-propylamine, (C$_3$H$_7$)$_2$NH;
(i) Pr$_3$N: tri-n-propylamine, (C$_3$H$_7$)$_3$N;
(j) Quin: Quinuclidine, (C$_7$H$_{13}$N);
(k) MQuin: Methyl Quinuclidine hydroxide, (C$_7$H$_{13}$NCH$_3$OH);
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Teraalkylorthosilicates, such as tetraethylorthosilicate;
(q) aluminum chlorhydrol.

Preparative Procedures

In some cases, it may be advantageous, when synthesizing the GeAPSO compositions, to first combine sources of germanium and aluminum, or of germanium, aluminum and silicon, to form a mixed germanium/aluminum or germanium/aluminum/silicon compound (this compound being typically a mixed oxide) and thereafter to combine this mixed compound with a source of phosphorus to form the final GeAPSO composition. Such mixed oxides may be prepared for example by hydrolyzing aqueous solutions containing germanium tetrachloride and aluminum chlorhydrol, or germanium ethoxide, tetraethylorthosilicate, and aluminum tri-sec-butoxide.

GeAPSOs may be prepared by forming a starting solution by dissolving the H$_3$PO$_4$ in at least part of the water. To this solution the aluminum isopropoxide or CATAPAL is added. This mixture is then blended until a homogeneous mixture is observed. To this mixture the templating agent and then a solution containing tetraethylorthosilicate and germanium ethoxide, and the resulting mixture blended until a homogeneous mixture is observed.

Alternatively, the phosphoric acid may first be mixed with the templating agent, and then a solution containing tetraethylorthosilicate and germanium ethoxide combined with the phosphoric acid/templating agent solution. Then the aluminum oxide is added and the resultant mixture blended until homogeneous.

In a third procedure, the phosphoric acid may first be mixed with the templating agent and water, and to the resultant solution is added the solid aluminum/silicon/germanium mixed oxide prepared as described above. The resultant mixture is then blended until homogeneous.

Whichever procedure is adopted, the final mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

LiAPSO MOLECULAR SIEVES

The LiAPSO molecular sieves of U.S. Ser. No. 599,952, filed Apr. 13, 1984, and U.S. Ser. No. 847,227 filed Apr. 2, 1986 have a framework structure of LiO$_2^{-3}$, AlO$_2^{-}$, PO$_2^{+}$ and SiO$_2$ tetrahedral units having units having an empirical chemical composition on an anhydrous basis expressed by the formula:

mR:(Li$_w$Al$_x$P$_y$Si$_z$)O$_2$ wherein "R" represents at least one organic templating agent present in the intracrystalline pore system; "m" represents the molar amount of "R" present per mole of (Li$_w$Al$_x$P$_y$Si$_z$)O$_2$ and has a value of zero to about 0.3, but is preferably not greater than 0.15; and "w", "x", "y" and "z" represent the mole fractions of the elements lithium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the LiAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the LiAPSO molecular sieves, the value of w+z is not greater than about 0.20.

Since the exact nature of the LiAPSO molecular sieves is not clearly understood at present, although all are believed to contain LiO$_2$ tetrahedra in the three-dimensional microporous crystal framework structure, it is advantageous to characterize the LiAPSO molecular sieves by means of their chemical composition. This is due to the low level of lithium present in certain of the LiAPO molecular sieves prepared to date which makes it difficult to ascertain the exact nature of the interaction between lithium, aluminum, phosphorus and silicon. As a result, although it is believed that LiO$_2$ tetrahedra are substituted isomorphously for AlO$_2$, PO$_2$ or SiO$_2$ tetrahedra, it is appropriate to characterize certain LiAPSO compositions by reference to their chemical composition in terms of the mole ratios of oxides.

LiAPSO compositions are generally synthesized by hydrothermal crystallization from a reaction mixture containing reactive sources of lithium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the LiAPSO product are obtained, usually a period of from several hours to several weeks. Typical effective times of from 2 hours to about 30 days, generally from about 4 hours to about 20 days, and preferably about 1 to about 10 days, have been observed. The product is recovered by any convenient method such as centrifugation or filtration.

In synthesizing the LiAPSO compositions, it is preferred to employ a reaction mixture composition expressed in terms of the molar ratios as follows:

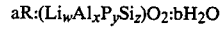

aR:(Li$_w$Al$_x$P$_y$Si$_z$)O$_2$:bH$_2$O wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20, and most desirably not greater than about 10; and "w", "x", "y" and "z" represent the mole fractions of lithium, aluminum, phosphorus and silicon, respectively, and each has a value of at least 0.01.

In one embodiment the reaction mixture is selected such that the mole fractions "w", "x", "y" and "z" are generally defined as being within the limiting composition values or points as follows:

| Point | Mole Fraction | | |
|---|---|---|---|
|  | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing lithium, aluminum, phosphorus and silicon as framework tetrahedral oxide units are prepared as follows:

Preparative Reagents

LiAPSO compositions may be prepared by using numerous reagents. Reagents which may be employed to prepare LiAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) lithium orthophosphate;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

LiAPSOs may be prepared by forming a starting reaction mixture mixing lithium phosphate and aluminum oxide, then adding the resultant mixture to the $H_3PO_4$. To the resultant mixture is added silica and the templating agent and the resulting mixture is blended until a homogeneous mixture is observed. The mixture is then placed in a lined (polytetrafluoroethylene) stainless steel pressure vessel and digested at a temperature (150° C. to 200° C.) for a time or placed in lined screw top bottles for digestion at 100° C. Digestions are typically carried out under autogenous pressure.

ALPO4 ALUMINOPHOSPHATE MOLECULAR SIEVES

The ALPO4 aluminophosphate molecular sieves of U.S. Pat. No. 4,310,440 are disclosed as microporous crystalline aluminophosphates having an essential crystalline framework structure whose chemical composition, expressed in terms of molar ratios of oxides, is:

$Al_2O_3$:0.8-1.2$P_2O_5$.

The pores of the framework structure are uniform and in each species have nominal diameters of from 3 to 10 Angstroms; the aluminophosphates have an intracrystalline adsorption capacity for water at 4.6 torr and 24° C. of at least 3.5 weight percent, the adsorption of water being completely reversible while retaining the same essential framework topology in both the hydrated and dehydrated state. By the term "essential framework topology" is meant the spatial arrangement of the primary Al-O and P-O bond linkages. No change in the framework topology indicates that there is no disruption of these primary bond linkages.

The aluminophosphates are prepared by hydrothermal crystallization of a reaction mixture prepared by combining a reactive source of phosphate, alumina and water and at least one structure-directing or templating agent which can include an organic amine and a quaternary ammonium salt. In the as-sytnthesized form, the structure-directing agent is contained within the framework structure of the aluminophosphate in amounts which vary from species to species but usually do not exceed one mole per mole of $Al_2O_3$ thereof. This structure-directing agent is readily removed by water washing or calcination and does not appear to be an essential constituent of the aluminophosphate, as evidenced by essentially complete absence of ion-exchangeability of the as-synthesized compositions and also the complete absence of any internally-contained organic molecules in the as-synthesized form of at least one species of the generic class. Evidence that structure-directing agent is a critical constituent is contained in certain of the Examples of the patent 4,310,440, wherein reaction mixtures, otherwise identical to those which yield the ALPO4 products except for the presence of templating agents, yield instead the previously known aluminophosphate phases ALPO4.I.I-1.3 $H_2O$, ALPO4-tridymite, ALPO4-quartz and ALPO4-cristobalite.

The ALPO4 aluminophosphates are prepared by forming a reaction mixture which contains, in terms of molar ratios of oxides:

$Al_2O_3$:0.5-1.5$P_2O_5$:7-100$H_2O$ and contains from about 0.2 to 2.0 moles of templating agent per mole of $Al_2O_3$. The reaction mixture is placed in a reaction vessel inert toward the reaction system and heated at a temperature of at least about 100° C., preferably between 100° C. and 300° C., until crystallized, usually a period from 2 hours to 2 weeks. The solid crystalline reaction product is then recovered by any convenient method, such as filtration or centrifugation, washed with water and dried at a temperature between ambient and 110° C., preferably in air.

MeAPO MOLECULAR SIEVES

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029. Members of this novel class of composition have a three-dimensional microporous crystal framework structure of $MO_2^{-2}$, $AlO_2^-$ and $PO_2^+$ tetrahedral units and have an essential empirical chemical composition, on an anhydrous basis, of:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y", and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y", "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as-synthesized compositions are capable of withstanding 350° C. calcination in air for extended periods, i.e., at least 2 hours, without becoming amorphous. While it is believed that the M, Al and P framework constituents are present in tetrahedral coordination with oxygen, it is theoretically possible that some minor fraction of these framework constituents are present in coordination with five or six oxygen atoms. It is not, moreover, necessarily the case that all of the M, Al and/or P content of any given synthesized product is a part of the framework in the aforesaid types of coordination with oxygen. Some of each constituent may be merely occluded or in some as yet undetermined form and may or may not be structurally significant.

Since the term "metal aluminophosphate" is somewhat cumbersome, particularly in view of the need for numerous repetitions thereof in describing such compositions, the "short-hand" reference "MeAPO" is employed hereinafter. Also in those cases where the metal "Me" in the composition is magnesium, the acronym MAPO is applied to the composition. Similarly, ZAPO, MnAPO, and CoAPO are applied to the compositions which contain zinc, manganese and cobalt, respectively. To identify the various structural species which make up each of the subgeneric classes MAPO, ZAPO, CoAPO and MnAPO, each species is assigned a number and is identified, for example, as ZAPO-5, MAPO-11, CoAPO-11 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion-exchange. Such ionic species, when present, function primarily as charge-balancing ions for $AlO^-_2$ and/or $MO^{-2}_2$ tetrahedra not associated with $PO^+_2$ tetrahedra or an organic ion derived from the organic templating agent.

The metal aluminophosphates ("MeAPOs") are synthesized by hydrothermal crystallization from a reaction mixture containing reactive sources of the metal "M", alumina and phosphate, an organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature between 100° C. and 225° C., and preferably between 100° C. and 200° C., until crystals of the metal aluminophosphate product are obtained, usually a period of from 4 hours to 2 weeks. The product is recovered by any convenient method such as centrifugation or filtration.

In synthesizing the MeAPO compositions, it is preferred to employ a reaction mixture composition expressed in terms of molar ratio as follows:

$$aR:(M_xAl_yP_z)O_2:bH_2O$$

wherein "R" is an organic templating agent; "a" has a value great enough to constitute an effective concentration of "R" and is within the range of >0 to 6; "b" has a value of from zero to 500, preferably 2 to 30; "M" represents a metal of the group zinc, magnesium, manganese and cobalt, "x", "y" and "z" represents the mole fractions, respectively, of "M", aluminum and phosphorus in the $(M_xAl_yP_z)O_2$ constituent, and each has a value of at least 0.01, the said points E, F, G, H, I, and J representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(M+Al+P)=(x+y+z)=1.00$ mole.

In forming the reaction mixture from which the metal aluminophosphates are crystallized the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorous, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N-N-dimethylethanolamine; choline; N,N'-dimethylpiperazine; 1,4-diazabicyclo (2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of metal aluminophosphate (MeAPO), i.e., a single templating agent can, with proper manipulation of the reaction conditions, direct the formation of several MeAPO compositions, and a given MeAPO composition can be produced using several different templating agents.

The preferred phosphorus source is phosphoric acid, but organic phosphates such as triethylphosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are no preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The metals zinc, cobalt, magnesium and manganese can be introduced into the reaction system in any form which permits the formation in situ of reactive divalent ions of the respective metals. Advantageously salts, oxides or hydroxides of the metals are employed such as cobalt chloride hexahydrate, alpha cobaltous iodide, cobaltous sulfate, cobalt acetate, cobaltous bromide, cobaltous chloride, zinc acetate, zinc bromide, zinc formate, zinc iodide, zinc sulfate heptahydrate, magnesium acetate, magnesium bromide, magnesium chloride, magnesium iodide, magnesium nitrate, magnesium sulfate, manganous acetate, manganous bromide, manganous sulfate, and the like.

While not essential to the synthesis of MeAPO compositions, it has been found that in general, stirring or other moderate agitation of the reaction mixture and/or seeding the reaction mixture with seed crystals of either the MeAPO species to be produced or a topologically similar aluminophosphate or aluminosilicate composition, facilitates the crystallization procedure.

After crystallization the MeAPO product is isolated and advantageously washed with water and dried in air. The as-synthesized MeAPO contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular MeAPO species. As a general rule, the templating agent, and hence the occluded organic species, is too large to move freely through the pore system of the MeAPO product and must be removed by calcining the MeAPO at temperatures of 200° C. to 700° C. to thermally degrade the organic species. In a few instances the pores of the MeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the MeAPO phase wherein the organic moiety occupying the intracrystalline pore system as a result of the hydrothermal crystallization process has been reduced by post-synthesis treatment such that the value of "m" in the composition formula:

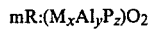

$$mR:(M_xAl_yP_z)O_2$$

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized MeAPO material.

Since the MeAPO compositions are formed from $AlO_2$, $PO_2$, and $MO_2$ tetrahedral units which, respectively, have a net charge of $-1$, $+1$, and $-2$, the matter of cation exchangeability is considerably more complicated than in the case of zeolitic molecular sieves in which, ideally, there is a stoichiometric relationship between $AlO_2$ tetrahedra and charge-balancing cations. In the MeAPO compositions, an $AlO_2^-$ tetrahedron can be balanced electrically either by association with a $PO_2^+$ tetrahedron or a simple cation such as an alkali metal cation, a cation of the metal "M" present in the reaction mixture, or an organic cation derived from the templating agent. Similarly an $MO_2^{-2}$ tetrahedron can be balanced electrically by association with $PO_2^+$ tetrahedra, a cation of the metal "M", organic cations derived from the templating agent, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$, respectively [Flanigen and Grose, Molecular Sieve Zeolites-I, ACS, Washington, D.C. (1971)].

FAPO MOLECULAR SIEVES

Ferroaluminophosphates are disclosed in U.S. Pat. No. 4,554,143, incorporated herein by reference, and have a three-dimensional microporous crystal framework structure of $AlO_2$, $FeO_2$, and $PO_2$ tetrahedral units and have an essential empirical chemical composition, on an anhydrous basis, of:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved; "x", "y", and "z" represent the mole fractions of iron, aluminum and phosphorus, respectively, present as tetrahedral oxides, representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the $FeO_2$ structural units can be in either the ferric or ferrous valence state, depending largely upon the source of the iron in the synthesis gel. Thus, an $FeO_2$ tetrahedron in the structure can have a net charge of either $-1$ or $-2$. While it is believed that the Fe, Al and P framework constituents are present in tetrahedral coordination with oxygen (and are referred to herein as such), it is theoretically possible that some minor fraction of these framework constituents are present in coordination with five or six oxygen atoms. It is not, moreover, necessarily the case that all of the Fe, Al and/or P content of any given synthesized product is a part of the framework in the aforesaid types of coordination with oxygen. Some of each constituent may be merely occluded or in some as yet undetermined form, and may or may not be structurally significant.

For convenience in describing the ferroaluminophosphates, the "short-hand" acronym "FAPO" is sometimes employed hereinafter. To identify the various structural species which make up the generic class FAPO, each species is assigned a number and is identified, for example, as FAPO-11, FAPO-31 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion-exchange. Such ionic species, when present, function primarily as charge-balancing ions for $FeO_2^-$ and/or $AlO_2^{-2}$ tetrahedra, $FeO_2^{-2}$ tetrahedra associated with $PO_2^+$ tetrahedra or not associated with $PO_2^+$ tetrahedra or an organic ion derived from the organic templating agent.

The aforesaid ferroaluminophosphates are synthesized by hydrothermal crystallization from a reaction mixture containing reactve sources of iron oxide, alumina and phosphate, or organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature of at least 100° C., and preferably between 100° C. and 250° C., until crystals of the metal aluminophosphate product are obtained, usually a period of from 2 hours to 2 weeks. The product is recovered by any convenient method such as centrifugation or filtration.

In synthesizing the FAPO compositions, it is preferred to employ a reaction mixture composition expressed in terms of molar ratios as follows:

$$aR:(Fe_xAl_yP_z)O_2:bH_2O$$

wherein "R" is an organic templating agent; "a" has a value great enough to constitute an effective concentration of "R" and is within the range of >0 to 6; "b" has a value of from zero to 500, preferably 2 to 80; "x", "y" and "z" represent the mole fractions, respectively, of iron, aluminum and phosphorus in the $(Fe_xAl_yP_z)O_2$ constituent, and each has a value of at least 0.01, and representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(Fe+Al+P)=(x+y+z)=1.00$ mole.

In forming the reaction mixture from which the ferroaluminophosphates are crystallized, the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the fromula $R_4N^+$ wherein each R is alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Mono-, di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tri-n-propylamine; triethylamine; triethanolamine; piperidine; cyclohexylamine; 2-methylpyridine; N,N-dimethylbenzylamine; N-N-dimethylethanolamine; choline; N,N'-dimethylpiperazine; 1,4-diazabicyclo(2,2,2)octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine; neopentylamine; di-n-pentylamine; isopropylamine; t-butylamine; ethylenediamine; pyrrolidine; and 2-imidazolidone. Not every templating agent will direct the formation of every species of ferroaluminophosphate (FAPO), i.e., a single templating agent can, with proper manipulation of the reaction conditions, direct the formation of several FAPO compositions, and a given FAPO composition can be produced using several different templating agents.

The phosphorus source is preferably phosphoric acid, but organic phosphates such as triethylphosphate have been found satisfactory, and so also have crystalline or amorphous aluminophosphates such as the AlPO$_4$ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

Iron can be introduced into the reaction system in any form which permits the formation in situ of reactive ferrous or ferric ions. Advantageously iron salts, oxides or hydroxides are employed such as iron sulfate, iron acetate, iron nitrate, or the like. Other sources such as a freshly precipitated iron oxide gamma-FeOOH, are also suitable.

While not essential to the synthesis of FAPO compositions, it has been found that in general, stirring or other moderate agitation of the reaction mixture and/or seeding the reaction mixture with seed crystals of either the FAPO species to be produced or a topologically similar aluminophosphate or aluminosilicate composition, facilitates the crystallization procedure.

After crystallization the FAPO product is isolated and advantageously washed with water and dried in air. The as-synthesized FAPO contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular FAPO species. As a general rule, the templating agent, and hence the occluded organic species, is too large to move freely through the pore system of the FAPO product and must be removed by calcining the FAPO at temperatures of 200° C. to 700° C. to thermally degrade the organic species. In a few instances the pores of the FAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the FAPO phase wherein the organic moiety occupying the intracrystalline pore system as a result of the hydrothermal crystallization process has been reduced by post-synthesis treatment such that the value of "m" in the composition formula:

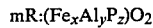

$$mR:(Fe_xAl_yP_z)O_2$$

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as-synthesized FAPO material.

Since the FAPO compositions are formed from $AlO_2^-$, $PO_2^+$, $FeO_2^-$ and/or $FeO_2^{-2}$ units the matter of cation exchangeability is considerably more complicated than in the case of zeolitic molecular sieves in which, ideally, there is a stoichiometric relationship between $AlO_2$ tetrahedra and charge-balancing cations. In the FAPO compositions, an $AlO_2^-$ tetrahedron can be balanced electrically either by association with a $PO_2^+$ tetrahedron or a simple cation such as an alkali metal cation, a $Fe^{+2}$ or $Fe^{+3}$ cation present in the reaction mixture, or an organic cation derived from the templating agent. Similarly an $FeO_2^-$ or $FeO_2^{-2}$ tetrahedron can be balanced electrically by association with $PO_2^+$ tetrahedron, a $Fe^{+2}$ or $Fe^{+3}$ cation, organic cations derived from the templating agent, or other metal cation introduced from an extraneous source. It has also been postulated that non-adjacent $AlO_2^-$ and $PO_2^+$ tetrahedral pairs can be balanced by $Na^+$ and $OH^-$, respectively [Flanigen and Grose, Molecular Sieve Zeolites-I, ACS, Washington, D.C. (1971)].

TAPO MOLECULAR SIEVES

TAPO molecular sieves are disclosed in U.S. Pat. No. 4,500,561, incorporated herein by reference, and comprise a three-dimensional microporous crystal framework structure of [TiO$_2$], [AlO$_2$] and [PO$_2$] tetrahedral units which has a unit empirical formula on an anhydrous basis of:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0, the maximum value in each case depending upon the molecular dimensions of the templating agent and the available void volume of pore system of the particular titanium molecular sieve; "x", "y" and "z" represent the mole fractions of titanium, aluminum and phosphorus, respectively, present as tetrahedral oxides, representing the following values for "x", "y" and "z":

|       | Mole Fraction |      |       |
|-------|-------|-------|-------|
| Point | x     | y     | z     |
| A     | 0.001 | 0.45  | 0.549 |
| B     | 0.88  | 0.01  | 0.11  |
| C     | 0.98  | 0.01  | 0.01  |
| D     | 0.29  | 0.70  | 0.01  |
| E     | 0.001 | 0.70  | 0.299 |

The parameters "x", "y" and "z" are preferably within the following values for "x", "y" and "z":

|       | Mole Fraction |      |       |
|-------|-------|-------|-------|
| Point | x     | y     | z     |
| a     | 0.002 | 0.499 | 0.499 |
| b     | 0.20  | 0.40  | 0.40  |
| c     | 0.20  | 0.50  | 0.30  |
| d     | 0.10  | 0.60  | 0.30  |
| e     | 0.002 | 0.60  | 0.398 |

The titanium-containing molecular sieves are referred to hereinafter, solely for point of reference herein as "TAPO" molecular sieves, or as "TAPOs" if the reference is to the class as a whole. This designation is simply made for the sake of convenient reference herein and is not meant to designate a particular structure for any given TAPO molecular sieve. The members of the class of TAPO's employed hereinafter in the examples will be characterized simply by referring to such members as TAPO-5, TAPO-11, etc, i.e., a particular species will be referred to as TAPO-n where "n" is a number specific to a given class member as its preparation is reported herein. This designation is an arbitrary one and is not intended to denote structural relationship to another material(s) which may also be characterized by a numbering system.

The term "unit empirical formula" is used herein according to its common meaning to designate the simplest formula which gives the relative number of moles of titanium, aluminum and phosphorus which form the [TiO$_2$], [PO$_2$] and [AlO$_2$] tetrahedral unit within a titanium-containing molecular sieve and which forms the molecular framework of the TAPO composition(s). The unit empirical formula is given in terms of titanium, aluminum and phosphorus as shown in Formula (1), above, and does not include other compounds, cations or anions which may be present as a result of the preparation or the existence of other impurities or materials in the bulk composition not containing the aforementioned tetrahedral unit. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of organic templating agent by the total moles of titanium, aluminum and phosphorus.

The unit empirical formula for a TAPO may be given on an "as-synthesized" basis or may be given after an "as-synthesized" TAPO composition has been subjected to some post treatment process, e.g., calcination. The term "as-synthesized" herein shall be used to refer to the TAPO composition(s) formed as a result of the hydrothermal crystallization but before the TAPO composition has been subjected to post treatment to remove any volatile components present therein. The actual value of "m" for a post-treated TAPO will depend on several factors (including: the particular TAPO, template, severity of the post-treatment in terms of its ability to remove the template from the TAPO, the proposed application of the TAPO composition, and etc.) and the value for "m" can be within the range of values as defined for the as-synthesized TAPO compositions although such is generally less than the as-synthesized TAPO unless such post-treatment process adds template to the TAPO so treated. A TAPO composition which is in the calcined or other post-treatment form generally has an empirical formula represented by Formula (1), except that the value of "m" is generally less than about 0.02. Under sufficiently severe post-treatment conditions, e.g., roasting in air at high temperature for long periods (over 1 hr.), the value of "m" may be zero (0) or, in any event, the template, R, is undetectable by normal analytical procedures.

The TAPO molecular sieves are generally further characterized by an intracrystalline adsorption capacity for water at 4.6 torr and about 24° C. of about 3.0 weight percent. The adsorption of water has been observed to be completely reversible while retaining the same essential framework topology in both the hydrated and dehydrated state. The term "essential framework topology" is meant to designate the spatial arrangement of the primary bond linkages. A lack of change in the framework topology indicates that there is no disruption of these primary bond linkages.

The TAPO molecular sieves are generally synthesized by hydrothermal crystallization from a reaction mixture comprising reactive sources of titanium, aluminum and phosphorus, and one or more organic templating agents. Optionally, alkali metal(s) may be present in the reaction mixture. The reaction mixture is placed in a pressure vessel, preferably lined with an inert plastic material, such as polytetrafluoroethylene, and heated, preferably under autogenous pressure, at a temperature of at least about 100° C., and preferably between 100° C. and 250° C., until crystals of the molecular sieve product are obtained, usually for a period of from 2 hours to 2 weeks. While not essential to the synthesis of the TAPO molecular sieves, it has been found that in general stirring or other moderate agitation of the reaction mixture and/or seeding the reaction mixture with seed crystals of either the TAPO to be produced, or a topologically similar composition, facilitates the crystallization procedure. The product is recovered by any convenient method such as centrifugation or filtration.

After crystallization the TAPO(s) may be isolated and washed with water and dried in air. As a result of the hydrothermal crystallization, the as-synthesized TAPO contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed TAPO and may be removed by a post-treatment process, such as by calcining the TAPO at temperatures of between about 200° C. and to about 700° C. so as to thermally degrade the template or by employing some other post-treatment process for removal of at least part of the template from the TAPO. In some instances the pores of the TAPO are sufficiently large to permit transport of the template, and, accordingly, complete or partial removal thereof can be accomplished by conventional desorption procedures such as carried out in the case of zeolites.

The TAPOs are preferably formed from a reaction mixture having a mole fraction of alkali metal cation which is sufficiently low that it does not interfere with the formation of the TAPO composition.

The TAPO compositions are generally formed from a reaction mixture containing reactive soureces of $TiO_2$, $Al_2O_3$, and $P_2O_5$ and an organic templating agent, said reaction mixture comprising a composition expressed in terms of molar oxide ratios of:

$fR_2O:(Ti_xAl_yP_z)O_2:gH_2O$ wherein "R" is an organic templating agent; "f" has a value large enough to constitute an effective amount of "R", said effective amount being that amount which form said TAPO compositions; "g" has a value of from zero to 500; "x", "y" and "z" represent the mole fractions, respectively of titanium, aluminum and phosphorus in the $(Ti_xAl_yP_z)O_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

Although the TAPO compositions will form if higher concentrations of alkali metal cation are present, such reaction mixtures are not generally preferred. A reaction mixture, expressed in terms of molar oxide ratios, comprising the following bulk composition is preferred:

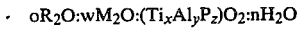

$oR_2O:wM_2O:(Ti_xAl_yP_z)O_2:nH_2O$ wherein "R" is an organic template; "o" has a value great enough to constitute an effective concentration of "R" and is preferably within the range of from greater than zero (0) to about 5.0; "M" is an alkali metal cation; "w" has a value of from zero to 2.5; "n" has a value between about zero (0) and about 500; "x", "y" and "z" represent the mole fractions, respectively, of titanium, aluminum and phosphorus in the $(Ti_xAl_yP_z)O_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

When the TAPOs are synthesized by this method the value of "m" in Formula (1) is generally above about 0.02.

Though the presence of alkali metal cations is not preferred, when they are present in the reaction mixture it is preferred to first admix at least a portion (e.g., at least about 10 weight percent) of each of the aluminum and phosphorus sources in the substantial absence (e.g., preferably less than about 20 percent of the total weight of the aluminum source and phosphorus source) of the titanium source. This procedure avoids adding the phosphorus source to a basic reaction mixture containing the titanium source and aluminum source, (as was done in most of the published attempts to substitute isomorphously $[PO_2]$ tetrahedra for $[SiO_2]$ tetrahedra in zeolitic structures). Although the reaction mechanism is by no means clear at this time, the function of the template may be to favor the incorporation of $[PO_2]$ and $[AlO_2]$ tetrahedra in the framework structures of the crystalline products with $[TiO_2]$ tetrahedra isomorphously replacing $[PO_2]$ tetrahedra.

The reaction mixture from which these TAPOs are formed contains one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and is desirably of the formula $R_4X^+$ wherein X is selected from the group consisting of nitrogen, phosphorus, arsenic and/or antimony and R may be hydrogen, alkyl, aryl, aralkyl, or alkylaryl group and is preferably aryl or alkyl containing between 1 and 8 carbon atoms, although more than eight carbon atoms may be present in the group "R" of the template. Nitrogen-containing templates are preferred, including amines and quaternary ammonium compounds, the latter being represented generally by the formula $R'_4N^+$ wherein each R' is an alkyl, aryl, alkylaryl, or araalkyl group; wherein R' preferably contains from 1 to 8 carbon atoms or higher when R' is alkyl and greater than 6 carbon atoms when R' is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and triamines, including mixed amines, may also be employed as templates either alone or in combination with a quaternary ammonium compound or another template. The exact relationship of various templates when concurrently employed is not clearly understood. Mixtures of two or more templating agents can produce either mixtures of TAPOs or in the instance where one template is more strongly directing than another template the more strongly directing template may control the course of the hydrothermal crystallization wherein with the other template serving primarily to establish the pH conditions of the reaction mixture.

Representative templates include tetramethylammonium, tetraethylammonium, tetrapropylammonium or tetrabutylammonium ions; di-n-propylamine; tri-propylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo(2,2,2)octane; N-methyldiethanolamine, N-methyl-ethanolamine; N-methylcyclohexylamine; 3-methyl-pyridine; 4-methylpyridine; quinuclidine; N,N'-dimethyl-1,4-diazabicyclo(2,2,2)octane ion; di-n-butylamine; neopentylamine; di-n-pentylamine; isopropylamine; t-butylamine; ethylenediamine; pyrrolidine; and 2-imidazolidone. Not every template will produce every TAPO composition although a single template can, with proper selection of the reaction conditions, cause the formation of different TAPO compositions, and a given TAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the TAPOs, although such may be acting as templates.

Alkali metal cations, if present in the reaction mixture, may facilitate the crystallization of certain TAPO phases, although the exact function of such cations, when present, in crystallization, if any, is not presently known. Alkali cations present in the reaction mixture generally appear in the formed TAPO composition, either as occluded (extraneous) cations and/or as structural cations balancing net negative charges at various sites in the crystal lattice. It should be undestood that although the unit formula for the TAPOs does not specifically recite the presence of alkali cations they are not excluded in the same sense that hydrogen cations and/or hydroxyl groups are not specifically provided for in the traditional formulae for zeolitic aluminosilicates.

Almost any reactive titanium source may be employed herein. The preferred reactive titanium sources include titanium alkoxides, water-soluble titanates and titanium chelates.

Almost any reactive phosphorous source may be employed. Phosphoric acid is the most suitable phosphorus source employed to date. Accordingly, other acids of phosphorus are generally believed to be suitable phosphorus sources for use herein. Organic phosphates such as triethyl phosphate have been found satisfactory, and so also have crystalline or amorphous aluminophosphates such as the $AlPO_4$ compositions of U.S. Pat. No. 4,130,440. Organo-phosphorus compounds, such as tetrabutyl-phosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g., esters, are believed to be generally suitable since they can generate acids of phosphorus in situ. Conventional phosphorus salts, such as sodium metaphosphate, may be used, at least in part as the phosphorus source, but they are not preferred.

Almost any reactive aluminum source may be employed herein. The preferred reactive aluminum sources include aluminum alkoxides, such as aluminum isopropoxide, and pseudoboehmite. Crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but as generally not preferred.

Since the exact nature of the TAPO molecular sieves are not clearly understood at present, although all are believed to contain $[TiO_2]$ tetrahedra in the three-dimensional microporous crystal framework structure, it is advantageous to characterize the TAPO molecular sieves by means of their chemical composition. This is due to the low level of titanium present in certain of the TAPO molecular sieves prepared to date which makes it difficult to ascertain the exact nature of the interaction between titanium, aluminum and phosphorus. As a result, although it is believed that titanium, $[TiO_2]$, has substituted isomorphously for $[AlO_2]$ or $[PO_2]$ tetrahedra, it is appropriate to characterize certain TAPO compositions by reference to their chemical composition in terms of the mole ratios of oxides in the as-synthesized and anhydrous form as:

$$vR:pTiO_2:qAl_2O_3:rP_2O_5$$

wherein "R" represents at least one organic templating agent present in the intracrystalline pore system; "v" represents an effective amount of the organic templating agent to form said TAPO compositions and preferably has a value between and including zero and about 3.0; "p", "q" and "r" represent moles, respectively, of titanium, alumina and phosphorus pentoxide, based on said moles being such that they are within the following values for "p", "q" and "r":

|       | Mole Fraction |     |        |
|-------|---------------|-----|--------|
| Point | x             | y   | z      |
| A     | 0.004         | 1.0 | 1.22   |
| B     | 176           | 1.0 | 11.0   |
| C     | 196           | 1.0 | 1.0    |
| D     | 0.828         | 1.0 | 0.0143 |
| E     | 0.003         | 1.0 | 0.427  |

The parameters "p", "q" and "r" are preferably within the following values for "p", "q" and "r":

|       | Mole Fraction |     |       |
|-------|---------------|-----|-------|
| Point | x             | y   | z     |
| a     | 0.008         | 1.0 | 1.0   |
| b     | 1.0           | 1.0 | 1.0   |
| c     | 0.80          | 1.0 | 0.60  |
| d     | 0.333         | 1.0 | 0.50  |
| e     | 0.067         | 1.0 | 0.663 |

ELAPO MOLECULAR SIEVES

"ELAPO" molecular sieves are a class of crystalline molecular sieves in which at least one element capable of forming a three-dimensional microporous framework forms crystal framework structures of $AlO_2^-$, $PO_2^+$ and $MO_2^n$ tetrahedral oxide units wherein "$MO_2^n$" represents at least one different element (other than Al or P) present as tetrahedral oxide units "$MO_2^n$" with charge "n" where "n" may be −3, −2, −1, 0 or +1. The members of this novel class of molecular sieve compositions have crystal framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2$$

wherein "R" represents at last one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different element ($M_1$) such that the molecular sieves contain at least one framework tetrahedral unit in addition to $AlO_2^-$ and $PO_2^+$. "M" is at least one element selected from the group consisting of arsenic, beryllium, boron, chromium, gallium, germanium and lithium, and when "M" denotes two elements the second element may be one of the aforementioned and/or is at least one element selected from the group consisting of cobalt, iron, magnesium, manganese, titanium and zinc. ELAPOs and their preparation are disclosed in European Patent Application Ser. No. 85104386.9, filed Apr. 11, 1985 (EPC Publication No. 0158976, published Oct. 13, 1985, incorporated herein by reference) and 85104388.5, filed Apr. 11, 1985 (EPC Publication No. 158349, published Oct. 16, 1985, incorporated herein by reference).

The "ELAPO" molecular sieves further include numerous species which are intended herein to be within the scope of the term "non-zeolitic molecular sieves" such being disclosed in the following copending and commonly assigned applications, incorporated herein by reference thereto [(A) following a serial number indicates that the application is abandoned, while (CIP) following a serial number indicates that the application is a continuation-in-part of the immediately preceding application, and (C) indicates that the application is a continuation of the immediately preceding application]:

| U.S. Ser. No. | Filed | NZMS |
|---|---|---|
| 600,166 (A) | April 13, 1984 | AsAPO |
| 830,889 (CIP) | Feb. 19, 1986 | AsAPO |
| 599,812 (A) | April 13, 1984 | BAPO |
| 804,248 (C) | Dec. 4, 1985 | BAPO |
| 599,776 (A) | April 13, 1984 | BeAPO |
| 835,293 (CIP) | March 3, 1986 | BeAPO |
| 599,813 (A) | April 13, 1984 | CAPO |
| 830,756 (CIP) | Feb. 19, 1986 | CAPO |
| 599,771 (A) | April 13, 1984 | GaAPO |
| 830,890 (CIP) | Feb. 19, 1986 | GaAPO |
| 599,807 (A) | April 13, 1984 | GeAPO |
| 841,753 (CIP) | March 20, 1986 | GeAPO |
| 599,811 (A) | April 13, 1984 | LiAPO |
| 834,921 (CIP) | Feb. 28, 1986 | LiAPO |
| 600,172 (A) | April 13, 1984 | ElAPO (M comprises two different elements) |
| 846.088 (CIP) | March 31, 1986 | |

The ELAPO molecular sieves are generally referred to herein by the acronym "ELAPO" to designate element(s) "M" in a framework of $AlO_2^-$, $PO_2^+$ and $MO_2^n$ tetrahedral oxide units. Actual class members will be identified by replacing the "EL" of the acronym with the elements present as $MO_2^n$ tetrahedral units. For example, "MgBeAPO" designates a molecular sieve comprised of $AlO_2^-$, $PO_2^+$, $MgO_2^{-2}$ and $BeO_2^{-2}$ tetrahedral units. To identify various structural species which make up each of the subgeneric classes, each species is assigned a number and is identified as "ELAPO-i" wherein "i" is an integer. The given species designation is not intended to denote a similarity in structure to any other species denominated by a similar identification system.

The ELAPO molecular sieves comprise at least one additional element capable of forming framework tetrahedral oxide units ($MO_2^n$) to form crystal framework structures with $AlO_2^-$ and $PO_2^+$ tetrahedral oxide units wherein "M" represents at least one element capable of forming tetrahedral units "$MO_2^n$" where "n" is −3, −2, −1, 0 or +1 and is at least one element selected from the group consisting of arsenic, beryllium, boron, chromium, gallium, germanium and lithium. When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed.

The ELAPO molecular sieves have crystalline three-dimensional microporous framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2;$$

wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M", aluminum and phosphorus are expressed by the empirical chemical formula (anhydrous):

$$mR:(M_xAl_yP_z)O_2$$

where "x", "y" and "z" represent the mole fractions of said "M", aluminum and phosphorus. The individual mole fractions of each "M" (or when M denotes two or more elements, $M_1$, $M_2$, $M_3$, etc.) may be represented by "$x_1$", "$x_2$", "$x_3$", etc. wherein "$x_1$", "$x_2$", and "$x_3$" etc. represent the individual mole fractions of elements $M_1$, $M_2$, $M_3$, and etc. for "M" as above defined. The values of "$x_1$", "$x_2$", "$x_3$", etc. are as defined for "x", hereinafter, where "$x_1$"+"$x_2$"+"$x_3$" ... ="x" and where $x_1$, $x_2$, $x_3$, etc. are each at least 0.01.

The ELAPO molecular sieves have crystalline three-dimensional microporous framework structures of $MO_2^n$, $AlO_2^-$ and $PO_2^+$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; in general, said mole fractions "x", "y" and "z" are within the following values for "x", "y" and "z", although as will appear hereinbelow, the limits for "x", "y" and "z" may vary slightly with the nature of the element "M":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

Also, in general, in a preferred sub-class of the ELAPOs of this invention, the values of "x", "y" and "z" in the formula above are within the following values for "x", "y" and "z", although again the relevant limits may vary somewhat with the nature of the element "M", as set forth hereinbelow:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

ELAPO compositions are generally synthesized by hydrothermal crystallization from a reaction mixture containing reactive sources of the elements "M", aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the ELAPO product are obtained, usually a period of from several hours to several weeks. Typical crystallization times are from about 2 hours to about 30 days with from about 2 hours to about 20 days being generally employed to obtain crystals of the ELAPO products. The product is recovered by any convenient method such as centrifugation or filtration.

In synthesizing the ELAPO compositions of the instant invention, it is in general preferred to employ a reaction mixture composition expressed in terms of the molar ratios as follows:

$$aR:(M_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; "M" represents at least one element, as above described, capable of forming tetrahedral oxide framework units, $MO_2{}^n$, with $AlO_2{}^-$ and $PO_2{}^+$ tetrahedral units; "n" has a value of $-3, -2, -1, 0$ or $+1$; and "x", "y" and "z" represent the mole fractions of "M", aluminum and phosphorus, respectively; "y" and "z" each have a value of at least 0.01 and "x" has a value of at least 0.01 with each element "M" having a mole fraction of at least 0.01. In general, the mole fractions "x", "y" and "z" are preferably within the following values for "x", "y" and "z":

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

Further guidance concerning the preferred reaction mixtures for forming ELAPOs with various elements "M" will be given below.

In the foregoing expression of the reaction composition, the reactants are normalized with respect to a total of $(M+Al+P)=(x+y+z)=1.00$ mole, whereas in other cases the reaction mixtures are expressed in terms of molar oxide ratios and may be normalized to 1.00 mole of $P_2O_5$ and/or $Al_2O_3$. This latter form is readily converted to the former form by routine calculations by dividing the total number of moles of "M", aluminum and phosphorus into the moles of each of "M", aluminum and phosphorus. The moles of template and water are similarly normalized by dividing by the total moles of "M", aluminum and phosphorus.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and triamines are advantageously utilized, either alone or in combination with a quaternary ammonium compound or other templating compound. Mixtures of two or more templating agents can either produce mixtures of the desired ELAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo(2,2,2,)octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ELAPO, i.e., a single templating agent can, with proper manipulation of the reaction conditions, direct the formation of several ELAPO compositions, and a given ELAPO composition can be produced using several different templating agents. The phosphorus source is preferably phosphoric acid, but organic phosphates such as triethyl phosphate may be satisfactory, and so also may crystalline or amorphous aluminophosphates such as the AlPO$_4$ composition of U.S. Pat. No. 4,310,440. Organophosphorus compounds, such as tetrabutylphosphonium bromide, do not apparently serve as reactive sources of phosphorus, but these compounds may function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The element(s) "M" can be introduced into the reaction system in any form which permits the formation in situ of reactive form of the element, i.e., reactive to form the framework tetrahedral oxide unit of the element. The organic and inorganic salts, of "M" such as oxides, alkoxides, hydroxides, halides and carboxylates, may be employed including the chlorides, bromides, iodides, nitrates, sulfates, phosphates, acetates, formates, and alkonixides, including ethoxides, propoxides and the like. Specific preferred reagents for introducing various elements "M" are discussed hereinbelow.

While not essential to the synthesis of ELAPO compositions, stirring or other moderate agitation of the reaction mixture and/or seeding the reaction mixture with seed crystals of either the ELAPO species to be produced or a topologically similar species, such as aluminophosphate, alumino-silicate or molecular sieve compositions, facilitates the crystallization procedure.

After crystallization the ELAPO product may be isolated and advantageously washed with water and dried in air. The as-synthesized ELAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular ELAPO species. As a general rule the templating agent, and hence the occluded organic species, is too large to move freely through the pore system of the ELAPO product and must be removed by calcining the ELAPO at temperatures of 200° C. to 700° C. to thermally degrade the organic species. In a few instances the pores of the ELAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the ELAPO phase wherein the organic moiety occupying the intracrystalline pore system as a result of the hydrothermal crystallization process has been reduced by post-synthesis treatment such that the value of "m" in the composition formula:

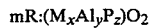

has a value of less than 0.02. The other symbols of the formula are as defined hereinabove. In those preparations in which an alkoxide is employed as the source of element "M", aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized ELAPO material.

Since the present ELAPO compositions are formed from $MO_2{}^n$, $AlO_2{}^-$ and $PO_2{}^+$ tetrahedral oxide units which, respectively, have a net charge of "n", (where "m" may be $-3$, $-2$, $-1$, 0 or $+1$), $-1$ and $+1$, the matter of cation exchangeability is considerably more complicated than in the case of zeolitic molecular sieves in which, ideally, there is a stoichiometric relationship between $AlO_2{}^-$ tetrahedra and charge-balancing cations. In the instant compositions, an $AlO_2{}^-$ tetrahedron can be balanced electrically either by association with a $PO_2{}^+$ tetrahedron or a simple cation such as an alkali metal cation, a proton ($H^+$), a cation of "M" present in the reaction mixture, or an organic cation derived from the templating agent. Similarly an $MO_2{}^n$ tetrahedron, where "n" is negative, can be balanced electrically by association with $PO_2{}^+$ tetrahedra, a cation of "M" present in the reaction mixture, organic cations derived from the templating agent, a simple cation such as an alkali metal cation, or other divalent or polyvalent metal cation, a proton ($H^+$), or anions or cations introduced from an extraneous source. It has also been postulated that non-adjacent $AlO_2{}^-$ and $PO_2{}^+$ tetrahedral pairs can be balanced by $Na^+$ and $OH^-$ respectively [Flanigen and Grose, Molecular Sieve Zeolites-I, ACS, Washington, DC (1971).

AsAPO MOLECULAR SIEVES

The AsAPO Molecular sieves of U.S. Ser. No. 600,166, filed Apr. 13, 1984, and U.S. Ser. No. 830,889 filed Feb. 19, 1986 have a framework structure of $AsO_2{}^n$, $AlO_2{}^-$ and $PO_2{}^+$ tetrahedral units (where "n" is $-1$ or $+1$) and have an empirical chemical composition on an anhydrous basis expressed by the formula:

$$mR:(As_xAl_yP_z)O_2$$

wherein "R" represents at least one organic templating agent present in the intracrystalline pore system; "m" represents the molar amount of "R" present per mole of $(As_xAl_yP_z)O_2$ and has a value of zero to about 0.3, but is preferably not greater than 0.15; and "x", "y" and "z" represent the mole fractions of the elements arsenic, aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

There are two preferred subclasses of the AsAPO molecular sieves, depending upon whether the value of "n" is −1 or +1 (i.e. whether the arsenic is trivalent or pentavalent), it being understood that mixtures of such are permitted in a given AsAPO. When "n" is −1, the preferred values of x, y and z are within the limiting compositional values or points as follows:

| Point | Mole Fraction | | |
|---|---|---|---|
| | x | y | z |
| a | 0.01 | 0.59 | 0.40 |
| b | 0.01 | 0.39 | 0.60 |
| c | 0.39 | 0.01 | 0.60 |
| d | 0.59 | 0.01 | 0.40 |

When "n" is +1, the preferred values of x, y and z are within the limiting compositional values or points as follows:

| Point | Mole Fraction | | |
|---|---|---|---|
| | x | y | z |
| e | 0.01 | 0.60 | 0.39 |
| f | 0.01 | 0.40 | 0.59 |
| g | 0.59 | 0.40 | 0.01 |
| h | 0.39 | 0.60 | 0.01 |

In an especially preferred subclass of the AsAPO molecular sieves in which "n"=+1, the values of x, y and z are as follows:

| Point | Mole Fraction | | |
|---|---|---|---|
| | x | y | z |
| i | 0.03 | 0.52 | 0.45 |
| j | 0.03 | 0.45 | 0.52 |
| k | 0.08 | 0.40 | 0.52 |
| l | 0.33 | 0.40 | 0.27 |
| m | 0.33 | 0.41 | 0.26 |
| n | 0.22 | 0.52 | 0.26 |

AsAPO compositions are generally synthesized by hydrothermal crystallization from a reaction mixture containing reactive sources of arsenic, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the AsAPO product are obtained, usually a period of from several hours to several weeks. Typical effective times of from 2 hours to about 30 days, generally from about 2 hours to about 20 days, and preferably about 12 hours to about 7 days, have been observed. The product is recovered by any convenient method such as centrifugation or filtration.

In synthesizing the AsAPO compositions, it is preferred to employ a reaction mixture composition expressed in terms of the molar ratios as follows:

$$aR:(As_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "x", "y" and "z" represent the mole fractions of arsenic, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixtures are those wherein the mole fractions "x", "y" and "z" are within the limiting compositional values or points as follows:

| Point | Mole Fraction | | |
|---|---|---|---|
| | x | y | z |
| a | 0.20 | 0.55 | 0.25 |
| b | 0.20 | 0.50 | 0.30 |
| c | 0.30 | 0.40 | 0.30 |
| d | 0.40 | 0.40 | 0.20 |
| e | 0.40 | 0.50 | 0.10 |
| f | 0.35 | 0.55 | 0.10 |

In the foregoing expression of the reaction composition, the reactants are normalized with respect to the total of "x", "y" and "z" such that (x+y+z)=1.00 mole. Molecular sieves containing arsenic, aluminum and phosphorus as framework tetrahedral oxide units are prepared as follows:

Preparative Reagents

AsAPO compositions may be prepared by using numerous reagents. Reagents which may be employed to prepare AsAPOs include:

(a) aluminum isopropoxide;
(b) pseudoboehmite or other aluminum oxide;
(c) $H_3PO_4$: 85 weight percent aqueous phosphoric acid;
(d) $As_2O_5$, arsenic (V) oxide;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

AsAPOs may be prepared by forming a starting reaction mixture by dissolving the arsenic(V) oxide and the $H_3PO_4$ in at least part of the water. To this solution the aluminum oxide or isopropoxide is added. This mixture is then blended until a homogeneous mixture is observed. To this mixture the templating agent and the resulting mixture blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BeAPO MOLECULAR SIEVES

The BeAPO molecular sieves of U.S. Ser. No. 599,776, filed Apr. 13, 1984, and U.S. Ser. No. 835,293 filed Mar. 3, 1986 have a framework structure of $BeO_2^{-2}$, $AlO_2^-$ and $PO_2^+$ tetrahedral units and have an empirical chemical composition on an anhydrous basis expressed by the formula:

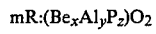

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3, but is preferably not greater than 0.15; and "x", "y" and "z" represent the mole fractions of the elements beryllium, aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |

-continued

| Point | Mole Fraction | | |
|---|---|---|---|
| | x | y | z |
| F | 0.39 | 0.60 | 0.01 |

In a preferred subclass of the BeAPO molecular sieves the values of x, y and z are within the limiting compositional values or points as follows:

| Point | Mole Fraction | | |
|---|---|---|---|
| | x | y | z |
| a | 0.01 | 0.60 | 0.39 |
| b | 0.01 | 0.39 | 0.60 |
| c | 0.35 | 0.05 | 0.60 |
| d | 0.35 | 0.60 | 0.05 |

In an especially preferred subclass of the BeAPO molecular sieves the values of x, y and z are as follows:

| Point | Mole Fraction | | |
|---|---|---|---|
| | x | y | z |
| e | 0.02 | 0.46 | 0.52 |
| f | 0.10 | 0.38 | 0.52 |
| g | 0.10 | 0.46 | 0.44 |

BeAPO compositions are generally synthesized by hydrothermal crystallization from a reaction mixture containing reactive sources of beryllium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BeAPO product are obtained, usually a period of from several hours to several weeks. Typical effective times of from 2 hours to about 30 days, generally from about 4 hours to about 14 days, and preferably about 1 to about 7 days, have been observed. The product is recovered by any convenient method such as centrifugation or filtration.

In synthesizing the BeAPO compositions, it is preferred to employ a reaction mixture composition expressed in terms of the molar ratios as follows:

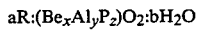

$$aR:(Be_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.5; "b" has a value of from zero (0) to about 500, preferably between about 2 and about 300, most preferably not greater than about 50; and "x", "y" and "z" represent the mole fractions of beryllium, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixtures are those wherein the mole fractions "x", "y" and "z" are within the limiting compositional values or points as follows:

| Point | Mole Fraction | | |
|---|---|---|---|
| | x | y | z |
| g | 0.04 | 0.46 | 0.50 |
| h | 0.16 | 0.34 | 0.50 |
| i | 0.17 | 0.34 | 0.49 |
| j | 0.17 | 0.43 | 0.40 |
| k | 0.14 | 0.46 | 0.40 |

In the foregoing expression of the reaction composition, the reactants are normalized with respect to the total of "x", "y" and "z" such that $(x+y+z)=1.00$ mole. Molecular sieves containing beryllium, aluminum and phosphorus as framework tetrahedral oxide units are prepared as follows:

Preparative Reagents

BeAPO compositions may be prepared by using numerous reagents. Reagents which may be employed to prepare BeAPOs include:
(a) aluminum isopropoxide;
(b) pseudoboehmite or other aluminum oxide;
(c) H3PO4: 85 weight percent aqueous phosphoric acid;
(d) beryllium sulfate;
(e) TEAOH: 40 weight percent aqueous solution of tetraethylammonium hydroxide;
(f) TBAOH: 40 weight percent aqueous solution of tetrabutylammonium hydroxide;
(g) Pr2NH: di-n-propylamine, (C3H7)2NH;
(h) Pr3N: tri-n-propylamine, (C3H7)3N;
(i) Quin: Quinuclidine, (C7H13N);
(j) MQuin: Methyl Quinuclidine hydroxide, (C7H13NCH3OH);
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

BeAPOs may be prepared by forming a starting reaction mixture by dissolving the beryllium sulfate and the H3PO4 in at least part of the water. To this solution the aluminum oxide or isopropoxide is added. This mixture is then blended until a homogeneous mixture is observed. To this mixture the templating agent and the resulting mixture blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogeneous pressure.

CAPO MOLECULAR SIEVES

The CAPO molecular sieves of U.S. Ser. No. 599,813, filed Apr. 13, 1984, and U.S. Ser. No. 830,756 filed Feb. 19, 1986 have a framework structure of $CrO_2{}^n$, $AlO_2{}^-$ and $PO_2{}^+$ tetrahedral units (where "n" is $-1$, 0 or $+1$) and have an empirical chemical composition on an anhydrous basis expressed by the formula:

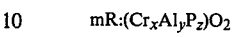

$mR:(Cr_xAl_yP_z)O_2$ wherein "R" represents at least one organic templating agent present in the intracrystalline pore system; "m" represents the molar amount of "R" present per mole of $(Cr_xAl_yP_z)O_2$ and has a value of zero to about 0.3, but is preferably not greater than 0.15; and "x", "y" and "z" represent the mole fractions of the elements chromium, aluminum and phosphorus, respectively, present as tetrahedral oxides. When "n" is $-1$ or $+1$, the mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

When "n" is 0, the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.47 | 0.52 |
| I | 0.94 | 0.01 | 0.05 |
| J | 0.98 | 0.01 | 0.01 |
| K | 0.39 | 0.60 | 0.01 |

There are three preferred subclasses of the CAPO molecular sieves, depending upon whether the value of "n" is $-1$, 0 or $+1$ (i.e. whether the chromium has an oxidation number of 3, 4 or 5), it being understood that mixtures of such are permitted in a given CAPO. When "n" is $-1$, the preferred values of x, y and z are within the limiting compositional values or points as follows:

| Point | Mole Fraction | | |
|---|---|---|---|
| | x | y | z |
| a | 0.01 | 0.59 | 0.40 |
| b | 0.01 | 0.39 | 0.60 |
| c | 0.39 | 0.01 | 0.60 |
| d | 0.59 | 0.01 | 0.40 |

In an especially preferred subclass of these CAPOS molecular sieves in which "n"=$-1$, the values of x, y and z are as follows:

| Point | Mole Fraction | | |
|---|---|---|---|
| | x | y | z |
| n | 0.01 | 0.52 | 0.47 |

-continued

| Point | Mole Fraction | | |
|---|---|---|---|
| | x | y | z |
| o | 0.01 | 0.42 | 0.57 |
| p | 0.03 | 0.40 | 0.57 |
| q | 0.07 | 0.40 | 0.53 |
| r | 0.07 | 0.47 | 0.46 |
| s | 0.02 | 0.52 | 0.46 |

When "n" is 0, the preferred values of x, y and z are within the limiting compositional values or points as follows:

| Point | Mole Fraction | | |
|---|---|---|---|
| | x | y | z |
| e | 0.01 | 0.60 | 0.39 |
| f | 0.01 | 0.47 | 0.52 |
| g | 0.50 | 0.225 | 0.275 |
| h | 0.50 | 0.40 | 0.10 |
| i | 0.30 | 0.60 | 0.10 |

When "n" is +1, the preferred values of x, y and z are within the limiting compositional values or points as follows:

| Point | Mole Fraction | | |
|---|---|---|---|
| | x | y | z |
| j | 0.01 | 0.60 | 0.39 |
| k | 0.01 | 0.40 | 0.59 |
| l | 0.59 | 0.40 | 0.01 |
| m | 0.39 | 0.60 | 0.10 |

Since the exact nature of the CAPO molecular sieves is not clearly understood at present, although all are believed to contain $CrO_2$ tetrahedra in the three-dimensional microporous crystal framework structure, it is advantageous to characterize the CAPO molecular sieves by means of their chemical composition. This is due to the low level of chromium present in certan of the CAPO molecular sieves prepared to date which makes it difficult to ascertain the exact nature of the interaction between chromium, aluminum and phosphorus. As a result, although it is believed that $CrO_2$ tetrahedra are substituted isomorphously for $AlO_2$ or $PO_2$ tetrahedra, it is appropriate to characterize certain CAPO compositions by reference to their chemical composition in terms of the mole ratios of oxides.

CAPO compositions are generally synthesized by hydrothermal crystallization from a reaction mixture containing reactive sources of chromium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogeneous pressure at a temperature between about 50° C. and about 250° C., and preferably between about 100° C. and about 200° C. until crystals of the CAPO product are obtained, usually a period of from several hours to several weeks. Typical effective times of from 2 hours to about 30 days, generally from about 2 hours to about 20 days, and preferably about 1 to about 10 days, have been observed. The product is recovered by any convenient method such as centrifugation or filtration.

In synthesizing the CAPO compositions, it is preferred to employ a reaction mixture composition expressed in terms of the molar ratios as follows:

$$aR:(C_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.6; "b" has a value of from zero (0) to about 500, preferably between about 2 and about 300, most preferably not greater than about 20; and "x", "y" and "z" represent the mole fractions of chromium, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| L | 0.01 | 0.60 | 0.39 |
| M | 0.01 | 0.39 | 0.60 |
| N | 0.39 | 0.01 | 0.60 |
| O | 0.98 | 0.01 | 0.01 |
| P | 0.39 | 0.60 | 0.01 |

Especially preferred reaction mixtures are those containing from about 0.1 to about 0.4 moles of chromium, and from about 0.75 to about 1.25 moles of aluminum, per mole of phosphorus.

In the foregoing expression of the reaction composition, the reactants are normalized with respect to the total "x", "y" and "z" such that $(x+y+z)=1.00$ mole. Molecular sieves containing chromium, aluminum and phosphorus as framework tetrahedral oxide units are prepared as follows:

Preparative Reagents

CAPO compositions may be prepared by using numerous reagents. Reagents which may be employed to prepare CAPOs include:

(a) aluminum isopropoxide, or aluminum chlorhydrol;
(b) pseudoboehmite or other aluminum oxide;
(c) $H_3PO_4$: 85 weight percent aqueous phosphoric acid;
(d) chromium(III) orthophosphate, chromium(III) acetate and chromium acetate hydroxide, $(Cr_3(OH)_2(CH_3COO)_7)$;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

CAPOs may be prepared by forming a starting reaction mixture by adding aluminum chlorhydrol or aluminum oxide to a solution of chromium acetate hydroxide in water, then adding successively phosphoric acid and the templating agent. Between each addition, and after formation of the final mixture, the mixture is blended until a homogeneous mixture is observed.

Alternatively, the phosphoric acid may be mixed with at least part of the water, and aluminum oxide or isopropoxide mixed in. A solution of chromium acetate hydroxide is then added, followed by the templating agent, and the resultant mixture mixed until homogeneous.

In a third procedure, amorphous chromium phosphate is ground dry with aluminum oxide and the resultant dry mixture added to an aqueous solution of phosphoric acid in an ice bath. The templating agent is then added, and the final mixture mixed until homogeneous.

Whichever technique is employed to produce the reaction mixture, this mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GaAPO MOLECULAR SIEVES

The GaAPO molecular sieves of U.S. Ser. No. 599,771, filed Apr. 13, 1984, and U.S. Ser. No. 830,890 filed Feb. 19, 1986 have a framework structure of $GaO_2^-$, $AlO_2^-$ and $PO_2^+$ tetrahedral units and have an empirical chemical composition on an anhydrous basis expressed by the formula:

$$mR:(Ga_xAl_yP_z)O_2$$

wherein "R" represents at least one organic templating agent present in the intracrystalline pore system; "m" represents the molar amount of "R" present per mole of $(Ga_xAl_yP_z)O_2$ and has a value of zero to about 0.3, but is preferably not greater than 0.15; and "x", "y" and "z" represent the mole fractions of the elements gallium, aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.34 | 0.65 |
| C | 0.34 | 0.01 | 0.65 |
| D | 0.60 | 0.01 | 0.39 |
| E | 0.60 | 0.39 | 0.01 |
| F | 0.39 | 0.60 | 0.01 |

In general, the value of "z" is the GaAPO molecular sieves is not greater than about 0.60.

In a preferred subclass of the GaAPO molecular sieves the values of x, y and z are within the limiting compositional values or points as follows:

| Point | Mole Fraction | | |
|---|---|---|---|
| | x | y | z |
| a | 0.01 | 0.59 | 0.40 |
| b | 0.01 | 0.34 | 0.65 |
| c | 0.34 | 0.01 | 0.65 |
| d | 0.59 | 0.01 | 0.40 |

In an especially preferred subclass of the GaAPO molecular sieves the values of x, y and z are as follows:

| Point | Mole Fraction | | |
|---|---|---|---|
| | x | y | z |
| e | 0.03 | 0.52 | 0.45 |
| f | 0.03 | 0.33 | 0.64 |
| g | 0.16 | 0.20 | 0.64 |
| h | 0.25 | 0.20 | 0.55 |
| i | 0.25 | 0.33 | 0.42 |
| j | 0.06 | 0.52 | 0.42 |

GaAPO compositions are generally synthesized by hydrothermal crystallization from a reaction mixture containing reactive sources of gallium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GaAPO product are obtained, usually a period of from several hours to several weeks. Typical effective times of about 2 hours to about 30 days, generally from about 4 hours to about 20 days, and preferably about 1 to about 7 days, have been observed. The product is recovered by any convenient method such as centrifugation or filtration.

In synthesizing the GaAPO compositions, it is preferred to employ a reaction mixture composition expressed in terms of the molar ratios as follows:

$$aR:(Ga_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably between about 2 and about 20; and "x", "y" and "z" represent the mole fractions of gallium, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |

| | Mole Fraction | | |
|---|---|---|---|
| Point | x | y | z |
| J | 0.98 | 0.01 | 0.01 |
| K | 0.39 | 0.60 | 0.01 |

Especially preferred reaction mixtures are those containing from 0.2 to 0.5 mole of $Ga_2O_3$ and from 0.3 to 1 mole of $Al_2O_3$ for each mole of $P_2O_5$.

In the foregoing expression of the reaction composition, the reactants are normalized with respect to the total "x", "y" and "z" such that $(x+y+z)=1.00$ mole. Molecular sieves containing gallium, aluminum and phosphorus as framework tetrahedral oxide units are prepared as follows:

Preparative Reagents

GaAPO compositions may be prepared by using numerous reagents. Reagents which may be employed to prepare GaAPOs include:

(a) aluminum isopropoxide;
(b) pseudoboehmite or other aluminum oxide;
(c) $H_3PO_4$: 85 weight percent aqueous phosphoric acid;
(d) gallium sulfate or gallium(III) hydroxide;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

GaAPOs may be prepared by forming a starting reaction mixture by mixing the phosphoric acid with at least part of the water. To this solution the aluminum oxide or isopropoxide is added. This mixture is then blended until a homogeneous mixture is observed. To this mixture the gallium sulfate or gallium hydroxide and the templating agent are successively added and the resulting mixture blended until a homogeneous mixture is observed.

Alternatively, the aluminum oxide may be mixed with a solution of the gallium sulfate or hydroxide, and then the phosphoric acid and the templating agent successively added. The resulting mixture is then blended until a homogeneous mixture is observed.

In a third process, the templating agent may be dissolved in water, the gallium hydroxide or sulfate added with stirring, a solution of the phosphoric acid added, and finally the aluminum oxide mixed in. The resulting mixture is then blended until a homogeneous mixture is observed.

Whichever technique is employed to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GeAPO MOLECULAR SIEVES

The GeAPO molecular sieves of U.S. Ser. No. 599,807, filed Apr. 13, 1984, and U.S. Ser. No. 841,753 filed Mar. 20, 1986 have a framework structure of $GeO_2$, $AlO_2^-$ and $PO_2^+$ tetrahedral units and have an empirical chemical composition on an anhydrous basis expressed by the formula:

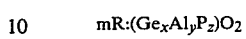

$$mR:(Ge_xAl_yP_z)O_2$$

wherein "R" represents at least one organic templating agent present in the intracrystalline pore system; "m" represents the molar amount of "R" present per mole of $(Ge_xAl_yP_z)O_2$ and has a value of zero to about 0.3, but is preferably not greater than 0.2; and "x", "y" and "z" represent the mole fractions of the elements germanium, aluminum and phosphorus, respectively, present as tetrahedral oxides. The mole fractions "x", "y" and "z" are generally defined as being within the limiting compositional values or points as follows:

| | Mole Fraction | | |
|---|---|---|---|
| Point | x | y | z |
| A | 0.01 | 0.60 | 0.39 |
| B | 0.01 | 0.47 | 0.52 |
| C | 0.94 | 0.01 | 0.05 |
| D | 0.98 | 0.01 | 0.01 |
| E | 0.39 | 0.60 | 0.01 |

In a preferred subclass of the GeAPO molecular sieves the values of x, y and z are within the limiting compositional values or points as follows:

| | Mole Fraction | | |
|---|---|---|---|
| Point | x | y | z |
| a | 0.01 | 0.60 | 0.39 |
| b | 0.01 | 0.47 | 0.52 |
| c | 0.50 | 0.225 | 0.275 |
| d | 0.50 | 0.40 | 0.10 |
| e | 0.30 | 0.60 | 0.10 |

An especially preferred subclass of the GeAPO molecular sieves are those in which the value of "x" is not greater than about 0.13.

GaAPO compositions are generally synthesized by hydrothermal crystallization from a reaction mixture containing reactive sources of germanium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GeAPO product are obtained, usually a period of from several hours to several weeks. Typical effective times of from 2 hours to about 30 days, generally from about 2 hours to about 20 days, and preferably about 1 to about 10 days, have been observed. The product is recovered by any convenient method such as centrifugation or filtration.

In synthesizing the GeAPO compositions, it is preferred to employ a reaction mixture composition expressed in terms of the molar ratios as follows:

$$aR:(Ge_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.6; "b" has a value of from zero (0) to about 500, preferably between about 2 and about 300, most preferably between about 10 and about 60; and "x", "y" and "z" represent the mole fractions of germanium, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

Especially preferred reaction mixtures are those containing from 0.2 to 0.4 mole of $GeO_2$ and from 0.75 to 1.25 mole of $Al_2O_3$ for each mole of $P_2O_5$.

In the foregoing expression of the reaction composition, the reactants are normalized with respect to the total of "x", "y" and "z" such that (x+y+z)=1.00 mole. Molecular sieves containing germanium, aluminum and phosphorus as framework tetrahedral oxide units are prepared as follows:

Preparative Reagents

GeAPO compositions may be prepared by using numerous reagents. Reagents which may be employed to prepare GeAPOs include:
(a) aluminum isopropoxide;
(b) pseudoboehmite or other aluminum oxide;
(c) $H_3PO_4$: 85 weight percent aqueous phosphoric acid;
(d) germanium tetrachloride, germanium ethoxide and germanium dioxide;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

In some cases, it may be advantageous, when synthesising the GeAPO compositions, to first combine sources of germanium and aluminum, to form a mixed germanium/aluminum compound (this compound being typically a mixed oxide) and thereafter to combine this mixed compound with a source of phosphorus to form the final GeAPO composition. Such mixed oxides may be prepared for example by hydrolyzing aqueous solutions containing germanium tetrachloride and aluminum chlorhydrol, or aluminum tri-sec-butoxide.

GeAPOs may be prepared by forming a starting reaction mixture by mixing the phosphoric acid with at least part of the water. To this solution is added the mixed germanium/aluminum oxide prepared as described above. This mixture is then blended until a homogeneous mixture is observed. To this mixture the templating agent is added and the resulting mixture blended until a homogeneous mixture is observed.

Alternatively, to a solution of aluminum isopropoxide may be added germanium ethoxide. The resultant solution may optionally be dried to produce a mixed oxide. To the mixed solution or dried oxide are added successively the phosphoric acid and the templating agent. The resulting mixture is then blended until a homogeneous mixture is observed.

In a third process, a solution is formed by dissolving the phosphoric acid in water, adding aluminum oxide or isopropoxide and mixing thoroughly. To the resultant mixture is added a solution containing the templating agent and germanium dioxide. The resulting mixture is then blended until a homogeneous mixture is observed.

Whichever technique is employed to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

LiAPO MOLECULAR SIEVES

The LiAPO molecular sieves of U.S. Ser. No. 599,811, filed Apr. 13, 1984, and U.S. Ser. No. 834,921 filed Feb. 28, 1986 have a framework structure of $Li-O_2^{-3}$, $AlO_2^-$ and $PO_2^+$ tetrahedral units and have an empirical chemical composition on an anhydrous basis expressed by the formula:

$$mR:(Li_xAl_yP_z)O_2$$

wherein "R" represents at least one organic templating agent present in the intracrystalline pore system; "m" represents the molar amount of "R" present per mole of $(Li_xAl_yP_z)O_2$ and has a value of zero to about 0.3, but is preferably not greater than 0.15; and "x", "y" and "z" represent the mole fractions of the elements lithium, aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

In a preferred subclass of the LiAPO molecular sieves the values of x, y and z are within the limiting compositional values or points as follows:

| | Mole Fraction | | |
|---|---|---|---|
| Point | x | y | z |
| a | 0.01 | 0.60 | 0.39 |
| b | 0.01 | 0.39 | 0.60 |
| c | 0.35 | 0.05 | 0.60 |
| d | 0.35 | 0.60 | 0.05 |

In an especially preferred subclass of the LiAPO molecular sieves the values of x, y and z are within the following limits:

| | Mole Fraction | | |
|---|---|---|---|
| Point | x | y | z |
| e | 0.01 | 0.52 | 0.47 |
| f | 0.01 | 0.47 | 0.52 |
| g | 0.03 | 0.45 | 0.52 |
| h | 0.10 | 0.45 | 0.45 |
| i | 0.10 | 0.49 | 0.41 |
| j | 0.07 | 0.52 | 0.41 |

LiAPO compositions are generally synthesized by hydrothermal crystallization from a reaction mixture containing reactive sources of lithium, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BeAPO product are obtained, usually a period of from several hours to several weeks. Typical effective times of from 2 hours to about 30 days, generally from about 12 hours to about 5 days, have been observed. The product is recovered by any convenient method such as centrifugation or filtration.

In synthesizing the LiAPO compositions, it is preferred to employ a reaction mixture composition expressed in terms of the molar ratios as follows:

aR:(Li$_x$Al$_y$P$_z$)O$_2$:bH$_2$O wherein "R" is an organic templating agent; "a" is the amount of organic templating agent "R" and has a value of from zero to about 6 and is preferably an effective amount within the range of greater than zero (0) to about 6, and most preferably not more than about 2; "b" has a value of from zero (0) to about 500, preferably between about 2 and about 300, most preferably not greater than about 40; and "x", "y" and "z" represent the mole fractions of lithium, aluminum and phosphorus, respectively, and each has a value of at least 0.01.

In one embodiment the reaction mixture is selected such that the mole fractions "x", "y" and "z" are generally defined as being within the limiting compositional values or points as follows:

| | Mole Fraction | | |
|---|---|---|---|
| Point | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

In an especially preferred subclass of the reaction mixtures, the values of "x", "y" and "z" are within the limiting compositional values or points as follows:

| | Mole Fraction | | |
|---|---|---|---|
| Point | x | y | z |
| l | 0.03 | 0.50 | 0.47 |
| m | 0.03 | 0.45 | 0.52 |
| n | 0.08 | 0.40 | 0.52 |
| o | 0.10 | 0.40 | 0.50 |
| q | 0.04 | 0.50 | 0.46 |

In the foregoing expression of the reaction composition, the reactants are normalized with respect to the total of "x", "y" and "z" such that (x+y+z)=1.00 mole.

Since the exact nature of the LiAPO molecular sieves is not clearly understood at present, although all are believed to contain LiO$_2$ tetrahedra in the three-dimensional microporous crystal framework structure, it is advantageous to characterize the LiAPO molecular sieves by means of their chemical composition. This is due to the low level of lithium present in certain of the LiAPO molecular sieves prepared to date which makes it difficult to ascertain the exact nature of the interaction between lithium, aluminum and phosphorus. As a result, although it is believed that LiO$_2$ tetrahedra are substituted isomorphously for AlO$_2$ or PO$_2$ tetrahedra, it is appropriate to characterize certain LiAPO compositions by reference to their chemical composition in terms of the mole ratios of oxides.

Molecular sieves containing lithium, aluminum and phosphorus as framework tetrahedral oxide units are prepared as follows:

Preparative Reagents

LiAPO compositions may be prepared by using numerous reagents. Reagents which may be employed to prepare LiAPOs include:
(a) aluminum isopropoxide;
(b) pseudoboehmite or other aluminum oxide;
(c) H$_3$PO$_4$: 85 weight percent aqueous phosphoric acid;
(d) lithium sulfate or lithium orthophosphate;
(e) TEAOH: 40 weight percent aqueous solution of tetraethylammonium hydroxide;
(f) TBAOH: 40 weight percent aqueous solution of tetrabutylammonium hydroxide;
(g) Pr$_2$NH: di-n-propylamine, (C$_3$H$_7$)$_2$NH;
(h) Pr$_3$N: tri-n-propylamine, (C$_3$H$_7$)$_3$N;
(i) Quin: Quinuclidine, (C$_7$H$_{13}$N);
(j) MQuin: Methyl Quinuclidine hydroxide, (C$_7$H$_{13}$NCH$_3$OH);
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

LiAPOs may be prepared by forming a starting reaction mixture by aluminum oxide in at least part of the water. To this mixture the templating agent is added. The resultant mixture is then blended until a homogeneous mixture is observed. To this mixture the lithium phosphate or sulfate is added and the resulting mixture blended until a homogeneous mixture is observed.

Alternatively, an initial mixture may be formed by mixing aluminum oxide and lithium phosphate or sulfate. To the resultant mixture are added successively phosphoric acid and an aqueous solution of the templating agent, and the resulting mixture blended until a homogeneous mixture is observed.

In a third procedure, the phosphoric acid is mixed with at least part of the water, and the amuminum oxide is mixed in. To the resultant mixture are added lithium sulfate and the templating agent, and the resulting mixture blended until a homogeneous mixture is observed.

Whichever procedure is adopted to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

MIXED-ELEMENT APO MOLECULAR SIEVES

The mixed element APO molecular sieves of U.S. Ser. No. 599,978, filed Apr. 13, 1984, and U.S. Ser. No. 846,088 filed Mar. 31, 1986 have a framework structure of $MO_2^n$, $AlO_2^-$ and $PO_2^+$ tetrahedral units, wherein $MO_2^n$ represents at least two different elements present as tetrahedral units "$MO_2^n$" with charge "n", where "n" may be $-3$, $-2$, $-1$, 0 or $+1$. One of the elements "M" is selected from the group consisting of arsenic, beryllium, boron, chromium, gallium, germanium, lithium and vanadium, while a second one of the elements "M" is selected from the group consisting of cobalt, iron, magnesium, manganese, titanium and zinc. Preferably, "M" is a mixture of lithium and magnesium. The mixed-element molecular sieves have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mol of $(Li_xAl_yP_z)O_2$ and has a value of zero to about 0.3, but is preferably not greater than 0.15; and "x", "y" and "z" represent the mole fractions of the elements "M" (i.e. "x" is the total of the mole fractions of the two or more elements "M"), aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of the mixed-element APO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

An especially preferred subclass of the mixed-element APO molecular sieves are those in which the value of x is not greater than about 0.10.

The mixed-element APO compositions are generally synthesized by hydrothermal crystallization from a reaction mixture containing reactive sources of the elements "M", aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the APO product are obtained, usually a period of from several hours to several weeks. Typical effective times of from 2 hours to about 30 days, generally from about 2 hours to about 20 days, and preferably about 12 hours to about 5 days, have been observed. The product is recovered by any convenient method such as centrifugation or filtration.

In synthesizing the mixed-element APO compositions, it is preferred to employ a reaction mixture composition expressed in terms of the molar ratios as follows:

$$aR:(M_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20, and most desirably not more than about 10; and "x", "y" and "z" represent the mole fractions of "M", aluminum and phosphorus, respectively, "y" and "z" each having a value of at least 0.01 and "x" having a value of at least 0.02, with each element "M" having a mole fraction of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.02 | 0.60 | 0.38 |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

Preferred reaction mixtures are those containing not more than about 0.2 moles of the metals "M" per mole of phosphorus.

In the foregoing expression of the reaction composition, the reactants are normalized with respect to the total of "x", "y" and "z" such that (x+y+z)=1.00 mole.

Since the exact nature of the mixed-element APO molecular sieves is not clearly understood at present, although all are believed to contain MO₂ tetrahedra in the three-dimensional microporous crystal framework structure, it is advantageous to characterize the mixed-element APO molecular sieves by means of their chemical composition. This is due to the low level of the elements "M" present in certain of the mixed-element APO molecular sieves prepared to date which makes it difficult to ascertain the exact nature of the interaction between the metals "M", aluminum and phosphorus. As a result, although it is believed that MO₂ tetrahedra are substituted isomorphously for AlO₂ for PO₂ tetrahedra, it is appropriate to characterize certain mixed-element APO compositions by reference to their chemical composition in terms of the mole ratios of oxides.

Molecular sieves containing the metals "M", aluminum and phosphorus as framework tetrahedral oxide units are prepared as follows:

Preparative Reagents

Mixed-element APO compositions may be prepared by using numerous reagents. Reagents which may be employed to prepare mixed-element APOs include:
(a) aluminum isopropoxide;
(b) pseudoboehmite or other aluminum oxide;
(c) H₃PO₄: 85 weight percent aqueous phosphoric acid;
(d) lithium phosphate or magnesium hydroxide or corresponding salts of the other elements "M";
(e) TEAOH: 40 weight percent aqueous solution of tetraethylammonium hydroxide;
(f) TBAOH: 40 weight percent aqueous solution of tetrabutylammonium hydroxide;
(g) Pr₂NH: di-n-propylamine, (C₃H₇)₂NH;
(h) Pr₃N: tri-n-propylamine, (C₃H₇)₃N;
(i) Quin: Quinuclidine, (C₇H₁₃N);
(j) MQuin: Methyl Quinuclidine hydroxide, (C₇H₁₃NCH₃OH);
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

Mixed element APOs may be prepared by forming a starting reaction mixture by mixing aluminum oxide, magnesium hydroxide, lithium phosphate (or the corresponding salts of the other elements "M"). To this mixture the phosphoric acid is added. The resultant mixture is then blended until a homogeneous mixture is observed. To this mixture the templating agent is added and the resulting mixture blended until a homogeneous mixture is observed.

The reaction mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

SILICOALUMINOPHOSPHATE MOLECULAR SIEVES

The preferred NZMSs, to date, are the silicoaluminophosphate molecular sieves described in U.S. Pat. No. 4,440,871. The use of such catalysts in reforming catalysts or as components in heretofore employed reforming/dehydrocyclization catalysts provides improved catalysts and provides products characterized by an improved selectivity to iso-products and provides improved activity in reforming/dehydrocyclization reactions.

The silicoaluminophosphate molecular sieves of U.S. Pat. No. 4,440,871 are disclosed as microporous crystalline silicoaluminophosphates, the pores of which are uniform and have nominal diameters of greater than about 3 Angstroms and whose essential empirical chemical composition in the as-synthesized and anhydrous form is:

mR:(Si$_x$Al$_y$P$_z$)O₂ wherein "R" represents at least one organic templating agent present in the intracrystalline pore system; "m" represents the moles of "R" present per mole of (Si$_x$Al$_y$P$_z$)O₂ and has a value of from 0.02 to 0.3; "x", "y" and "z" represent the mole fractions of silicon, aluminum and phosphorus, respectively, present as tetrahedral oxides, said mole fractions being such that they are within the pentagonal compositional area defined by points A, B, C, D and E of the ternary diagram of FIG. 5 of the aforementioned U.S. Pat. No. 4,440,871, and are preferably within the pentagonal compositional area defined by points a, b, c, d and e of FIG. 6 of this patent. The SAPO molecular sieves of U.S. Pat. No. 4,440,871 are also described as silicoaluminophosphates having a three-dimensional microporous framework structure of PO₂⁺, AlO₂⁻ and SiO₂ tetrahedral units, and whose essential empirical chemical composition on an anhydrous basis is:

mR:(Si$_x$Al$_y$P$_z$)O₂ wherein "R" represents at least one organic templating agent present in the intracrystalline pore system; "m" represents the moles of "R" present per mole of (Si$_x$Al$_y$P$_z$)O₂ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5 of the aforementioned patent, said silicoaluminophosphate having a characteristic X-ray powder diffraction pattern which contains at least the d-spacings set forth below in any one of Tables I, III, V, VII, IX, XIII, XVII, XXI, XXIII or XXV of U.S. Pat. No. 4,440,871. Further, the as-synthesized crystalline silicoaluminophosphates of U.S. Pat. No. 4,440,871 may be calcined at a temperature sufficiently high to remove at least some of any organic templating agent present in the intracrystalline pore system as a result of such synthesis. The silicoaluminophosphates of U.S. Pat. No. 4,440,871 are generally referred to therein as "SAPO", as a class, or as "SAPO-n" wherein "n" is an integer denoting a particular SAPO as its preparation is reported in U.S. Pat. No. 4,440,871. The preparation of the SAPOs is disclosed in U.S. Pat. No. 4,440,871, incorporated herein by reference.

Medium pore (MP)-SAPOs include SAPO-11, SAPO-31, SAPO-40 and SAPO-41.

The species SAPO-11 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5 of the patent, and preferably within the area bounded by points a, b, c, d and e on the ternary diagram which is FIG. 6 of the patent, said silicoaluminophosphate having a characteristic X-ray powder diffraction pattern which contains at least the d-spacings set forth below:

| SAPO-11 | | |
|---|---|---|
| 2θ | d(Å) | Relative Intensity |
| 9.4–9.65 | 9.41–9.17 | m |
| 20.3–20.6 | 4.37–4.31 | m |
| 21.0–21.3 | 4.23–4.17 | vs |
| 21.1–22.35 | 4.02–3.99 | m |
| 22.5–22.9 (doublet) | 3.95–3.92 | m |
| 23.15–23.35 | 3.84–3.81 | m–s |

The species SAPO-31 are referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5 of the patent, and preferably within the area bounded by points a, b, c, d and e on the ternary diagram which is FIG. 6 of the patent, said silicoaluminophosphate having a characteristic X-ray powder diffraction pattern which contains at least the d-spacings set forth below:

| SAPO-31 | | |
|---|---|---|
| 2θ | d(Å) | Relative Intensity |
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |

| SAPO-31 | | |
|---|---|---|
| 2θ | d(Å) | Relative Intensity |
| 31.7–31.8 | 2.823–2.814 | w–m |

The species SAPO-41 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5 of the patent, or preferably within the area bounded by points a, b, c, d and e on the ternary diagram which is FIG. 6 of the patent, said silicoaluminophosphate having a characteristic X-ray powder diffraction pattern which contains at least the d-spacings set forth below:

| SAPO-41 | | |
|---|---|---|
| 2θ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.44 | w–m |

NZMS-CONTAINING ISOMERIZATION CATALYSTS

The specific NZMSs employed in the instant invention are characterized in their calcined form by an adsorption of isobutane of at least 2 percent by weight, preferably at least 4 percent by weight, at a partial pressure of 500 torr and a temperature of 20° C. NZMSs characterized by the above described adsorption of isobutane include, but are not limited to, ELAPSO-5, ELAPSO-11, ELAPSO-31, ELAPSO-36, ELAPSO-37, ELAPSO-40, ELAPSO-41, SAPO-5, SAPO-11, SAPO-31, SAPO-36, SAPO-37, SAPO-40, SAPO-41, CoAPSO-5, CoAPSO-11, CoAPSO-31, CoAPSO-36, CoAPSO-37, CoAPSO-40, CoAPSO-41, FeAPSO-5, FeAPSO-11, FeAPSO-31, FeAPSO-36. FeAPSO-37, FeAPSO-40, FeAPSO-41, MgAPSO-5, MgAPSO-11, MgAPSO-31, MgAPSO-36, MgAPSO-37, MgAPSO-40, MgAPSO-41, MnAPSO-5, MnAPSO-11, MnAPSO-31, MnAPSO-36, MnAPSO-37, MnAPSO-40, MnAPSO-41, TiAPSO-5, TiAPSO-11, TiAPSO-31, TiAPSO-36, TiAPSO-37, TiAPSO-40, TiAPSO-41, ZnAPSO-5, ZnAPSO-11, ZnAPSO-31, ZnAPSO-36, ZnAPSO-37, ZnAPSO-40, ZnAPSO-41, CoMnAPSO-5, CoMnAPSO-11, CoMnAPSO-36, CoMnAPSO-37, CoMnAPSO-40, CoMnAPSO-41, CoMnMgAPSO-5, CoMnMgAPSO-11, CoMnMgAPSO-31, CoMnMgAPSO-36, CoMnMgAPSO-37, CoMnMgAPSO-40, CoMnMgAPSO-41, AsAPSO-5, AsAPSO-11, AsAPSO-31, AsAPSO-36, AsAPSO-37, AsAPSO-40, AsAPSO-41, BAPSO-5, BAPSO-11, BAPSO-31, BAPSO-36, BAPSO-37, BAPSO-40, BAPSO-41, BeAPSO-5, BeAPSO-11, BeAPSO-31, BeAPSO-36, BeAPSO-37, BeAPSO-40, BeAPSO-41, CAPSO-5, CAPSO-11, CAPSO-31, CAPSO-36, CAPSO-37, CAPSO-40, CAPSO-41, GaAPSO-5, GaAPSO-11, GaAPSO-31, GaAPSO-36, GaAPSO-37, GaAPSO-40, GaAPSO-41, GeAPSO-5, GeAPSO-11, GeAPSO-31, GeAPSO-36, GeAPSO-37, GeAPSO-40, GeAPSO-41, LiAPSO-5, LiAPSO-11, LiAPSO-31, LiAPSO-36, LiAPSO-37, LiAPSO-40, LiAPSO-41, MeAPO-5, MeAPO-11, MeAPO-31, MeAPO-36, MeAPO-37, MeAPO-40, MeAPO-41, TiAPO-5, TiAPO-11, TiAPO-31, TiAPO-36, TiAPO-37, TiAPO-40, TiAPO-41, FCAPO-5, FCAPO-11, FCAPO-31, FCAPO-36, FCAPO-37, FCAPO-40, FCAPO-41, AsAPO-5, AsAPO-11, AsAPO-31, AsAPO-36, AsAPO-37, AsAPO-40, AsAPO-41, BAPO-5, BAPO-11, BAPO-31, BAPO-36, BAPO-37, BAPO-40, BAPO-41, BeAPO-5, BeAPO-11, BeAPO-31, BeAPO-36, BeAPO-37, BeAPO-40, BeAPO-41, CAPO-5, CAPO-11, CAPO-31, CAPO-36, CAPO-37, CAPO-40, CAPO-41, GaAPO-5, GaAPO-11, GaAPO-31, GaAPO-36, GaAPO-37, GaAPO-40, GaAPO-41, GeAPO-5, GeAPO-11, GeAPO-31, GeAPO-36, GeAPO-37, GeAPO-40, GeAPO-41, LiAPO-5, LiAPO-11, LiAPO-31, LiAPO-36, LiAPO-37, LiAPO-40, LiAPO-41, and the mixed-element APOs which may be designated MAPO-5, MAPO-11, MAPO-31, MAPO-36, MAPO-37, MAPO-40 and MAPO-41, and mixtures thereof.

The above characterization of the NZMSs employed in the instant invention relates to an adsorption characterization that is carried out on a NZMS which has been subjected to a post synthesis treatment, e.g., calcination or chemical treatment, to remove a substantial portion of the template "R" which is present as a result of synthesis. Although a particular NZMS is characterised herein by reference to its adsorption of isobutane as being to the adsorption characteristics of the NZMS in its calcined form, the instant invention necessarily includes the use of a non-calcined or modified NZMSs which may be characterized by such adsorption in its calcined form, since upon use of such a non-calcined NZMS in the instant process at effective isomerization process conditions the NZMS may be calcined or hydrothermally treated in situ so as to have the characteristic adsorption of isobutane. Thus, the NZMS may be rendered in situ to a form characterized by the aforementioned adsorption characteristics. For example, an as-synthesized MgAPO-11 or MgAPSO-11 may not be characterized by the aforementioned adsorption of isobutane due to the presence of template "R" which is present as a result of synthesis, although the calcined form of MgAPO-11 and MgAPSO-11 will be characterized by the aforementioned adsorption of isobutane. Thus, reference to a NZMS having a particular adsorption characteristic in its calcined or anhydrous form is not intended to exclude the use of the NZMS in its as-synthesized form which upon in-situ calcination, hydrothermal treatment and/or other treatment, e.g., ion exchange with suitable atoms, would have such adsorption characteristics.

I claim:

1. A process for condensing a first ketone with a second ketone, which process comprises contacting the first and second ketones in the presence of hydrogen gas with a non-zeolitic molecular sieve, the non-zeolitic molecular sieve having, in its calcined form, an adsorption of isobutane of at least about 2 percent by weight of the non-zeolitic molecular sieve at a partial pressure of 500 torr and a temperature of 20° C., and with a hydrogenation catalyst capable of catalyzing the hydrogenation of an ethylenic unsaturation in an ethylenically unsaturated ketone, the contacting of the ketones with the hydrogenation catalyst and the non-zeolitic molecular sieve being effected under conditions effective to cause condensation of the first and second ketones and reaction with the hydrogen to form a saturated ketone.

2. A process according to claim 1 wherein the non-zeolitic molecular sieve has, in its calcined form, an adsorption of isobutane of at least about 4 percent by weight of the non-zeolitic molecular sieve at a partial pressure of 500 torr and a temperature of 20° C.

3. A process according to claim 1 wherein the non-zeolitic molecular sieve comprises a silicoaluminophosphate molecular sieve as claimed in U.S. Pat. No. 4,440,871.

4. A process according to claim 3 wherein the silicoaluminophosphate molecular sieve comprises any one or more of SAPO-5, SAPO-11, SAPO-31, SAPO-36, SAPO-37, SAPO-40 and SAPO-41.

5. A process according to claim 4 wherein the silicoaluminophosphate molecular sieve comprises SAPO-5.

6. A process according to claim 4 wherein the silicoaluminophosphate molecular sieve comprises SAPO-11.

7. A process according to claim 4 wherein the silicoaluminophosphate molecular sieve comprises SAPO-41.

8. A process according to claim 1 wherein the non-zeolitic molecular sieve comprises a silicoaluminophosphate molecular comprising at least one element capable of forming a framework tetrahedral oxide and selected from the group consisting of arsenic, beryllium, boron, chromium, cobalt, gallium, germanium, iron, lithium, magnesium, manganese, titanium and zinc.

9. A process according to claim 8 wherein the silicoaluminophosphate molecular sieve is a titanium silicoaluminophosphate molecular sieve wherein the mole fractions "w", "x", "y" and "z" of titanium, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39. |

10. A process according to claim 9 wherein the titanium silicoaluminophosphate molecular sieve comprises TiAPSO-5.

11. A process according to claim 8 wherein the silicoaluminophosphate molecular sieve is a magnesium silicoaluminosphosphate molecular sieve wherein the mole fractions "w", "x", "y" and "z" of magnesium, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

12. A process according to claim 8 wherein the silicoaluminophosphate molecular sieve is a manganese silicoaluminophosphate molecular sieve wherein the mole fractions "w", "x", "y" and "z" of manganese, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

13. A process according to claim 12 wherein the silicoaluminophosphate molecular sieve comprises MnAPSO-11.

14. A process according to claim 8 wherein the silicoaluminophosphate molecular sieve is a cobalt silicoaluminophosphate molecular sieve wherein the mole fractions "w", "x", "y" and "z" of cobalt, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

15. A process according to claim 14 wherein the silicoaluminophosphate molecular sieve comprises CoAPSO-11.

16. A process according to claim 8 wherein the silicoaluminophosphate molecular sieve is a zinc silicoaluminophosphate molecular sieve wherein the mole fractions "w", "x", "y" and "z" of zinc, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

17. A process according to claim 8 wherein the silicoaluminophosphate molecular sieve is an iron silicoaluminophosphate molecular sieve wherein the mole fractions "w", "x", "y" and "z" of iron, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

18. A process according to claim 17 wherein the silicoaluminophosphate molecular sieve comprises FeAPSO-5.

19. A process according to claim 8 wherein the silicoaluminophosphate molecular sieve is a cobalt-/manganese silicoaluminophosphate molecular sieve wherein the mole fractions "u", "v", "x", "y" and "z" of cobalt, manganese, aluminum, phosphorus and silicon, respectively, present as tetrahedral oxides each have a value of at least 0.01, the mole fractions "u", "v", "x", "y" and "z" being within the pentagonal compositional area defined by points A, B, C, D and E, said points A, B, C, D and E representing the following values for "w", "x", "y" and "z", where w=u+v:

| Point | Mole Fraction | | |
|---|---|---|---|
| | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

20. A process according to claim 8 wherein the silicoaluminophosphate molecular sieve is a cobalt-/manganese/magnesium silicoaluminophosphate molecular sieve wherein the mole fractions "t", "u", "v", "x", "y" and "z" of cobalt, manganese, magnesium, aluminum, phosphorus and silicon, respectively, present as tetrahedral oxides each have a value of at least 0.01, the mole fractions "t", "u", "v", "x", "y" and "z" being within the pentagonal compositional area defined by points A, B, C, D and E, said points A, B, C, D and E representing the following values for "w", "x", "y" and "z" (where w=t+u+v):

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39. |

21. A process according to claim 8 wherein the silicoaluminophosphate molecular sieve is an arsenic silicoaluminophosphate molecular sieve wherein the mole fractions "w", "x", "y" and "z" of arsenic, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

22. A process according to claim 8 wherein the silicoaluminophosphate molecular sieve is a boron silicoaluminophosphate molecular sieve wherein the mole fractions "w", "x", "y" and "z" of boron aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

23. A process according to claim 8 wherein the silicoaluminophosphate molecular sieve is a beryllium silicoaluminophosphate molecular sieve wherein the mole fractions "w", "x", "y" and "z" of beryllium, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

24. A process according to claim 8 wherein the silicoaluminophosphate molecular sieve is a chromium silicoaluminophosphate molecular sieve wherein the mole fractions "w", "x", "y" and "z" of chromium, aluminum, phosphorous and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

25. A process according to claim 8 wherein the silicoaluminophosphate molecular sieve is a gallium silicoaluminophosphate molecular sieve wherein the mole fractions "w", "x", "y" and "z" of gallium, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

26. A process according to claim 8 wherein the silicoaluminophosphate molecular sieve is a germanium silicoaluminophosphate molecular sieve wherein the mole fractions "w", "x", "y" and "z" of germanium, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

27. A process according to claim 8 wherein the silicoaluminophosphate molecular sieve is a lithium silicoaluminophosphate molecular sieve wherein the mole fractions "w", "x", "y" and "z" of lithium, aluminum, phosphorus and silicon, respectively, present as tetrahedral oxides each have a value of at least 0.01, the mole fractions "w", "x", "y" and "z" being within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

28. A process according to claim 1 wherein the nonzeolitic molecular sieve comprises an aluminophosphate molecular sieve as claimed in U.S. Pat. No. 4,310.440.

29. A process according to claim 28 wherein the aluminophosphate molecular sieve comprises any one or more of AlPO$_4$-5, AlPO$_4$-11 and AlPO$_4$-31.

30. A process according to claim 29 wherein the aluminophosphate molecular sieve comprises AlPO$_4$-31.

31. A process according to claim 1 wherein the nonzeolitic molecular sieve comprises an aluminophosphate molecular sieve as claimed in U.S. Pat. No. 4,567,029.

32. A process according to claim 31 wherein the aluminophosphate molecular sieve comprises MgAPO-36.

33. A process according to claim 1 wherein the nonzeolitic molecular sieve comprises an iron aluminophosphate molecular sieve as claimed in U.S. Pat. No. 4,554,143.

34. A process according to claim 1 wherein the nonzeolitic molecular sieve comprises a titanium aluminophosphate molecular sieve as claimed in U.S. Pat. No. 4,500,651.

35. A process according to claim 1 wherein the nonzeolitic molecular sieve comprises an aluminophosphate molecular sieve containing at least one element "M" capable of forming a framework tetrahedral oxide, the element "M" being selected from the group consisting of arsenic, beryllium, boron, chromium, gallium, germanium and lithium, subject to the proviso that, when "M" denotes two elements the second element is selected from the group consisting of arsenic, beryllium, boron, chromium, gallium, germanium, lithium, cobalt, iron, magnesium, manganese, titanium and zinc.

36. A process according to claim 35 wherein the aluminophosphate molecular sieve is an arsenic aluminophosphate molecular sieve wherein the mole fractions "x", "y" and "z" of arsenic, aluminum and phosphorus, respectively, present as tetrahedral oxides each have a value of at least 0.01, the mole fractions "x", "y" and "z" being within the hexagonal compositional area defined by points A, B, C, D, E and F, said points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01. |

37. A process according to claim 35 wherein the aluminophosphate molecular sieve is a boron aluminophosphate molecular sieve wherein the mole fractions "x", "y" and "z" of boron, aluminum and phosphorus, respectively, present as tetrahedral oxides each have a value of at least 0.01, the mole fractions "x", "y" and "z" being within the pentagonal compositional area defined by points A, B, C, D and E, the points A, B, C, D and E representing the following values for "x", "y" and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01. |

38. A process according to claim 35 wherein the aluminophosphate molecular sieve is a beryllium aluminophosphate molecular sieve wherein the mole fractions "x", "y" and "z" of beryllium, aluminum and phosphorus, respectively, present as tetrahedral oxides each have a value of at least 0.01, the mole fractions "x", "y" and "z" being within the hexagonal compositional area defined by points A, B, C, D, E and F, the points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01. |

39. A process according to claim 35 wherein the aluminophosphate molecular sieve is a chromium aluminophosphate molecular sieve wherein the mole fraction of chromium is at least 0.01.

40. A process according to claim 35 wherein the aluminophosphate molecular sieve is a gallium aluminophosphate molecular sieve wherein the mole fractions "x", "y" and "z" of gallium, aluminum and phosphorus, respectively, present as tetrahedral oxides each have a value of at least 0.01, the mole fractions "x", "y" and "z" being within the hexagonal compositional area defined by points A, B, C, D, E and F, the points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.34 | 0.65 |
| C | 0.34 | 0.01 | 0.65 |
| D | 0.60 | 0.01 | 0.39 |
| E | 0.60 | 0.39 | 0.01 |
| F | 0.39 | 0.60 | 0.01. |

41. A process according to claim 35 wherein the aluminophosphate molecular sieve is a germanium aluminophosphate molecular sieve wherein the mole fractions "x", "y" and "z" of germanium, aluminum and phosphorus, respectively, present as tetrahedral oxides each have a value of at least 0.01, the mole fractions "x", "y" and "z" being within the pentagonal compositional area defined by points A, B, C, D and E, the points A, B, C, D and E representing the following values for "x", "y" and "z":

| Point | Mole Fraction | | |
|---|---|---|---|
| | x | y | z |
| A | 0.01 | 0.60 | 0.39 |
| B | 0.01 | 0.47 | 0.52 |
| C | 0.94 | 0.01 | 0.05 |
| D | 0.98 | 0.01 | 0.01 |
| E | 0.39 | 0.60 | 0.01. |

42. A process according to claim 35 wherein the aluminophosphate molecular sieve is a lithium aluminophosphate molecular sieve wherein the mole fractions "x", "y" and "z" of lithium, aluminum and phosphorus, respectively, present as tetrahedral oxides each have a value of at least 0.01, the mole fractions "x", "y" and "z" being within the hexagonal compositional area defined by points A, B, C, D, E and F, the points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01. |

43. A process according to claim 35 wherein the aluminophosphate molecular sieve is a mixed-element aluminophosphate molecular sieve having a framework structure of $MO_2^n$, $AlO_2^-$ and $PO_2^+$ tetrahedral units, wherein $MO_2^n$ represents at least two different elements present as tetrahedral units "$MO_2^n$" with charge "n", where "n" may be −3, −2, −1, 0 or +1, one of the elements "M" being selected from the group consisting of arsenic, beryllium, boron, chromium, gallium, germanium, lithium and vanadium, while a second one of the elements "M" is selected from the group consisting of cobalt, iron, magnesium, manganese, titanium and zinc, and wherein the mole fractions "x", "y" and "z" of the elements "M", aluminum and phosphorus, respectively, present as tetrahedral oxides each have a value of at least 0.02, 0.01 and 0.01, respectively, the mole fractions "x", "y" and "z" being within the pentagonal compositional area defined by points A, B, C, D and E, the points A, B, C, D and E representing the following values for "x", "y" and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01. |

44. A process according to claim 1 wherein each of the first and second ketones contains three or four carbon atoms.

45. A process according to claim 44 wherein both the first and second ketones are acetone and the condensation product comprises at least one of methyl isobutyl ketone and diisobutyl ketone.

46. A process according to claim 45 which is carried out at a pressure of from about atmospheric pressure to about 1000 psig.

47. A process according to claim 45 which is carried out at a temperature of from about 150° C. to about 350° C.

48. A process according to claim 45 which is carried out at a weight hourly space velocity of liquid acetone in the range of from about 0.1 to about 50.

49. A process according to claim 48 which is carried out at a weight hourly space velocity of liquid acetone in the range of from about 0.5 to about 5.0.

50. A process according to claim 1 wherein the hydrogenation catalyst comprises a transition metal selected from the group consisting of copper, nickel, cobalt, palladium, platinum, rhodium and iridium.

51. A process according to claim 50 wherein the transition metal catalyst comprises nickel or platinum.

52. A process according to claim 50 wherein the transition metal catalyst comprises palladium.

53. A process according to claim 50 wherein the transition metal catalyst is incorporated into the non-zeolitic molecular sieve.

54. A process according to claim 53 wherein the transition metal catalyst is palladium and is present in the non-zeolitic molecular sieve in an amount of from about 0.01 to about 5 percent by weight of the non-zeolitic molecular sieve.

55. A process according to claim 54 wherein the palladium is present in the non-zeolitic molecular sieve in an amount of from about 0.1 to about 1 percent by weight of the non-zeolitic molecular sieve.

56. A process according to claim 1 wherein at least one of the ketones is formed in situ by feeding to the process a precursor compound capable of being converted to the at least one ketone and providing a precursor catalyst effective, under the reaction conditions, to convert the precursor compound to the at least one ketone.

57. A process according to claim 56 wherein the precursor compound comprises a compound capable of being dehydrogenated to yield at least one ketone, and the precursor catalyst comprises a dehydrogenation catalyst.

58. A process according to claim 57 wherein the precursor compound comprises a secondary alcohol which is dehydrogenated to form the ketone.

59. A process according to claim 58 wherein the precursor compound comprises isopropanol.

60. A process according to claim 59 wherein the non-zeolitic molecular sieve comprises a silicoaluminophosphate molecular sieve as claimed in U.S. Pat. No. 4,440,871.

61. A process according to claim 60 wherein the non-zeolitic molecular sieve comprises SAPO-5.

* * * * *